%

US008071653B2

(12) United States Patent
Aberg et al.

(10) Patent No.: US 8,071,653 B2
(45) Date of Patent: *Dec. 6, 2011

(54) USE OF RR/SR-RACTOPAMINE

(75) Inventors: A. K. Gunnar Aberg, Sarasota, FL (US); Karl Reuter, Gundelfingen (DE); Viktor Meier, Gundelfingen (DE); Florian Stolz, Denzlingen (DE); Eliso Gogritchiani, Freiburg (DE)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/751,134

(22) Filed: Mar. 31, 2010

(65) Prior Publication Data
US 2010/0184865 A1      Jul. 22, 2010

Related U.S. Application Data

(63) Continuation of application No. 12/221,780, filed on Aug. 6, 2008, now Pat. No. 7,723,392.

(60) Provisional application No. 61/005,214, filed on Dec. 3, 2007, provisional application No. 61/005,688, filed on Dec. 8, 2007.

(51) Int. Cl.
*A61K 31/135* (2006.01)
(52) U.S. Cl. .......................... 514/651; 514/653
(58) Field of Classification Search .................. 514/651, 514/653
See application file for complete search history.

(56) References Cited

U.S. PATENT DOCUMENTS

| | | | |
|---|---|---|---|
| 4,690,951 | A | 9/1987 | Anderson et al. |
| 4,992,473 | A | 2/1991 | Anderson et al. |
| 5,057,427 | A | 10/1991 | Wald et al. |
| 5,077,217 | A | 12/1991 | Matson et al. |
| 5,395,962 | A | 3/1995 | Kawashima |
| 5,545,745 | A | 8/1996 | Gao et al. |
| 5,643,967 | A | 7/1997 | Anderson et al. |
| 6,372,799 | B1 | 4/2002 | Aberg |
| 6,855,334 | B2 | 2/2005 | Bhatt et al. |
| 6,974,587 | B2 | 12/2005 | Trompen et al. |
| 7,723,392 | B2 * | 5/2010 | Aberg et al. .................. 514/651 |
| 7,985,775 | B2 | 7/2011 | Aberg |
| 2005/0113456 | A1 | 5/2005 | Aberg |
| 2007/0282010 | A1 | 12/2007 | Aberg |

FOREIGN PATENT DOCUMENTS

| | | |
|---|---|---|
| EP | 0 007 205 | 1/1980 |
| WO | 2006/064283 | 6/2006 |

OTHER PUBLICATIONS

J Allergy Clin. Immunol. Mar. 2004; vol. 113; No. 3; pp. 503-510; Agrawal et al.; "(S)-Albuterol activates pro-constrictory and pro-inflammatory pathways in human bronchial smooth muscle cells".
J Allergy Clin. Immunol. vol. 109, No. 3; Mar. 2002; pp. 449-454; Baramki et al.; "Modulation of T-cell function by (R)- and (S)-isomers of albuterol: Anti-inflammatory influences of (R)-isomers are negated in the presence of the (S)-isomer".
Biochimie (1992) 74, 267-273; RG Bardsley et al.; "Effect of β-agonists on expression of calpain and calpastatin activity in skeletal muscle".
Circulation Research vol. 59, No. 3, Sep. 1986; pp. 297-309; Bristow et al.; "β1-and β2-Adrenergic-Receptor Subpopulations in Nonfailing and Failing Human Ventricular Myocardium: Coupling of Both Receptor Subtypes to Muscle Contraction and Selective β1-Receptor Down-Regulation in Heart Failure".
J Pharm Pharmacol, Dec. 1991; 43(12): 844-7; Colbert WE et al.; "Beta-adrenoceptor profile of ractopamine HC1 in isolated smooth and cardiac muscle tissues of rat and guinea-pig"-abstract.
USDA International Egg and Poultry Revue, Aug. 2, 2005. www.ams.usda.gov/poultry/mncs/InterantionalPoultryandEgg/2005Reports/x080205.pdg.
Naunyn Schmiedebergs Arch Pharmacol. 2004; 369:525-32. Epub Apr. 2, 2004.; Joseph SS Lynham et al.; "Binding of (-)-[3H]-CGP12177 at two sites in recombinant human beta 1-adrenoceptors and interaction with beta-blockers"-Abstract.
Journal of Biological Chemistry; vol. 277, No. 34, Issue of Aug. 23, 2002; pp. 30429-30435; Malin C. Levin et al.; "The myocardium-protective Gly-49 Variant of the β1-Adrenergic Receptor Exhibits Constitutive Activity and Increased Desensitization and Down-regulation".
J. Anim. Sci. 2003. 81: 416-422; J.N. Marchant-Forde et al.; "The effects of ractopamine on the behavior and physiology of finishing pigs 1,2".
Poultry Science 82: 31-35; 2003; F.M. Odeh et al.; "Genetic Characterization of Stress Responsiveness in Japanese Quail. 2. Analyses of Maternal Effects, Additive Sex Linkage Effects, Heterosis, and Heritability by Diallel Crosses".
J.Anim. Sci. 1990 68: 3633-3641; Olayiwola Adeola et al.; "Manipulation of Porcine Carcass Composition by Ractopamine".
Poultry Science 2003 82: 1313-1318; J.Post et al.; "Physiological Effects of Elevated Plasma Corticosterone Concentrations in Broiler Chickens. An Alternative Means by Which to Assess the Physiological Effects of Stress".
Purdue University Animal Sciences Meat Quality and Safety; http://ag.ansc.purdue.edu/meat-quality/mqf-stress.html; date printed Aug. 5, 2008.
J.Anim.Sci. 1999. 77: 701-707; E.A. Ricke et al.; "Effects of Ractopamine HC1 Stereoisomers on Growth, Nitrogen Retention, and Carcass Composition in Rats".
Commercial Swine Production 2005; London, CJ et al. "Effects of a New Growth Promoter (R-albuterol) for Commercial Swine Production".
J.Anim.Sci 80, 2002, (E. Suppl. 2): E28-E32; S.E. Mills; "Biological basis of the ractopamine response".
J.Anim.Sci 2003, 81: 122-129; S.E. Mills et al.; "Stereoselectivity of porcine β-adrenergic receptors for ractopamine stereoisomers".

(Continued)

Primary Examiner — Raymond Henley, III
(74) Attorney, Agent, or Firm — Nields, Lemack & Frame, LLC

(57) ABSTRACT

A method of promoting weight loss in animals or humans by administering thereto a therapeutically effective amount of a mixture of RR-ractopamine and SR-ractopamine is disclosed.

12 Claims, No Drawings

OTHER PUBLICATIONS

J. Anim. Sci 2003, 81: 662-668; S.E. Mills et al.; β-Adrenergic receptor subtypes that mediate ractopamine stimulation of lipolysis.

J. Anim. Sci. 2000, 78: 699-708; N.W. Shappell et al.; "Response of C2C12 mouse and turkey skeletal muscle cells to the β-adrenergic agonist ractopamine".

Br.J.Pharmacol 1993), 109, 1157-1163; Martin N. Sillence et al.; "Ligand binding properties of putative β3-adrenoceptors compared in brown adipose tissue and in skeletal muscle membranes".

J.Anim.Sci. 1998. 76: 173-194; D.J. Smith; "The Pharmacokinetics, Metabolism, and Tissue Residues of β-Adrenergic Agonists in Livestock".

Sterle J.: The Frequency of the Porcine Stress Gene in Texas Show Pigs. 2005. http://animalscience.tamu.edu.

The University of Tennessee, Agricultural Extension Service, PB 1606; Stalder K.; "Porcine Stress Syndrome and Its Effects on Maternal, Feedlot and Carcass Quantitative and Qualitative Traits".

Clin. Pharmacol. Ther. vol. 28, No. 3, Sep. 1980; pp. 324-334; Michael J. Thompson et al.; "Hemodynamic effects of Intravenous Butopamine in Congestive Heart Failure".

Ractopamine; 2004; Ungemach F.R.: WHO Food Additives Series: 53; pp. 119-164; www.inchem.org/documents/jecfa/jecmono/v53je08.htm#bi3.

Merk Index, 1996, 12: Ractopamine: pp. 1392-1393.

J.Anim.Sci 1990. 68; 3588-3595; L.E. Watkins et al.; "The Effect of Various Levels of Ractopamine Hydrochloride on the Performance and Carcass Characteristics of Finishing Swine".

J.Anim.Sci 1994 72: 3152-3162; N.H. Williams et al.; "The Impact of Ractopamine, Energy Intake, and Dietary Fat on Finisher Pig Growth Performance and Carcass Merit".

The International Search Report date Nov. 4, 2008.

Goodman & Gilman's The Pharmacological Basis of Therapeutics Ninth Edition; B-Addrenergic Agnosts—pp. 212-216.

J.Anim. Sci. 1994, 72: 75-80; M.E. Spurlock et al.; "The Effect of Ractopamine on β-Adrenoceptor Density and Affinity in Porcine Adipose and Skeletal Muscle Tissue".

www.pfizerah.com/slentrol 9-pages—Slentrol (dirlotapide)—The First Prescription Weight-Loss Medication for Drugs.

Recueil 92 (1973) pp. 1281-1297; J. Van Dijk et al.; "Synthesis of B-Phenylethylamine derivatives X1* N-(Hydroxy- and Methoxy-Aralkyl) Derivatives".

11th Edition of Merk Index 1989: relevant pages/sections: p. 1444/s9098; p. 37/s.209; p. 625/s.3927; p. 744/s.4628; p. 1310/s.8223; p. 813/2.5053; p. 933/s.5836; p. 12941s.8142; p. 366/s.2347; p. 1231/s.7765; p. 278/s.1840; p. 15431 s.9729; p. 200/s.1317; p. 1190/s.7461; and p. 633/644/s.4159.

International Preliminary Examination Report in corresponding PCT/US08/09428 dated Jan. 22, 2010.

Office Actions dated Nov. 19, 2009 and Notice of Allowance dated Mar. 1, 2010 in parent U.S. Appl. No. 12/221,780.

Meat Science 38 (1994), pp. 329-340, "Relationships between Subjective and Objective Assessments of Stress at Slaughter and Meat Quality in Pigs", Warriss, P. D., et al.

* cited by examiner

USE OF RR/SR-RACTOPAMINE

This application is a continuation of U.S. Ser. No. 12/221,780, now U.S. Pat. No. 7,723,392, filed on Aug. 6, 2008, which claims priority of provisional application Ser. No. 61/005,214 filed on Dec. 3, 2007 and Ser. No. 61/005,688 filed on Dec. 8, 2007, the disclosures of which are hereby incorporated by reference.

FIELD OF THE INVENTION

The present invention relates to methods of improving the muscle-to-fat ratio in an animal, promoting or improving the growth of an animal and/or improving the feed efficiency of animals by administering therapeutically active isomers of the adrenergic beta-receptor agonist ractopamine to the animals in a quantity which is effective for this purpose. The invention further relates to compositions for use in the methods and to animal feed additives, which comprise one or more therapeutically active isomers of ractopamine as the active substance. The present invention refers to the use of RR/SR-ractopamine for repartitioning of livestock animals, for weight-loss of obese companion animals and for bronchodilation in horses, suffering from heaves. The present invention also includes a new and cost-effective manufacturing method for obtaining RR/SR-ractopamine from RR/SS/RS/SR-ractopamine.

BACKGROUND OF THE INVENTION

The pharmacological activities of all beta-adrenergic receptor agonists have one feature in common as they all activate adrenergic beta-receptors. Activation of adrenergic beta-receptors leads to increased intracellular concentration of cyclic adenosine monophosphate (cAMP), which triggers various events in various cells and organs. Cellular responses to beta-receptor activation include for example lipolytic activity in adipose tissues, smooth muscle relaxant activity of bronchial smooth muscle and increased frequency of contractions in the heart (Goodman-Gilman, The Pharmacological Basis of Therapeutics.) Most adrenergic beta-receptor agonists have affinity for two types of adrenergic beta-receptors. Thus, both salbutamol and ractopamine have affinity for adrenergic beta-1 and beta-2 receptors, but negligible affinity for beta-3 receptors (Example 2). There is no significant effect of ractopamine on adrenergic alpha-receptors according to Colbert et al., 1991, which publication is hereby included in its entirety by reference.

Adrenergic beta-agonistic drugs characteristically contain as part of their chemical structure an ethanolamine or 2-amino-ethanol moiety. Since the chemical structures of these drugs usually comprise at least one asymmetric carbon atom, these drugs commonly exist in optically active isomeric form, with the chiral carbon atom having (R) or (S) configuration. When there is one single asymmetric carbon atom present, the beta-receptor agonists exist as individual (R) or (S) enantiomers or in racemic (RS) form, i.e. as an approximately 50:50 mixture of (R) and (S) enantiomers. Compounds with two chiral centers—such as ractopamine—have four isomers, which are the RR-, SS-, RS-, and SR-isomers. For the sake of simplicity, RR-ractopamine may herein be referred to as RR or (RR), SS-ractopamine may herein be referred to as SS or (SS), RS-ractopamine may herein be referred to as RS or (RS), and SR-ractopamine may herein be referred to as SR or (SR). Compounds with four isomers (e.g. ractopamine) may exist in a number of forms i.e. in the single, pure RR or SS or RS or SR isomeric forms, or as mixtures of the compositions RR/SS, RR/SR, RR/RS or RS/SR, SR/SS or RS/SS. The compound ractopamine is a mixture of all four isomers. The term "optically pure isomer" or the like, as used herein, refers to a compound that contains at least 95% by weight of one isomer while the total concentration (i.e. the sum) of the corresponding and remaining isomers is 5% or less by weight, based on the total amount of ractopamine present.

RR/SS/RS/SR-ractopamine is a mixture of all four isomers in approximately similar concentrations. All four isomers usually exist in approximately the same concentrations of is approximately 25%. However, for the present purpose, RR/SS/RS/SR-ractopamine may contain from 23% to 27% of any of the four isomers.

Ractopamine has the molecular formula $C_{18}H_{23}NO_3$ and is typically prepared as a hydrochloride salt. Chemically, ractopamine differs from dobutamine in the location of only one hydroxyl group, but ractopamine is not a catecholamine and is therefore not instantaneously metabolised by catechol-O-methyl transferase. Ractopamine HCl (4-hydroxy-a-[[[3-(4-hydroxyphenyl)-1-methylpropyl]amino]methyl]benzenemethanol hydrochloride) has a molecular weight of 337.85 and a molecular formula of $C_{18}H_{23}NO_3.HCl$ (CAS number: 90274-24-1). The term ractopamine HCl refers to the hydrochloride salt of RR/SS/RS/SR-ractopamine. Thus, Ractopamine HCl (or ractopamine HCl) is the hydrochloride salt of a mixture of all four isomers in approximately equal proportions, as defined above.

The structure below depicts ractopamine. The two chiral centers (sites) are marked with asterisks (*). In order to differentiate between the two chiral centers (sites), they are here being called the "OH-site", which is the benzylic stereocenter, and the "Me-site" (FIG. 1). Thus RR-ractopamine has the R-configuration at both sites, while SR-ractopamine has the S-configuration at the "OH-site" and the R-configuration at the "Me-site".

FIG. 1. Chemical structure of ractopamine HCl; Isomers

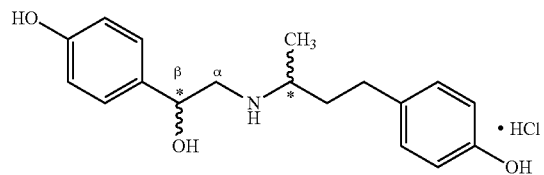

| Isomers: | Chiral sites | |
|---|---|---|
| | "OH-site" "benzylic site" | "Me-site" |
| RR | R | R |
| SR | S | R |
| SS | S | S |
| RS | R | S |

Ractopamine is commercially available under the trade names PAYLEAN®, Elanco and OPTAFLEX®, Elanco and both are used as growth promotants for livestock.

Although structurally identical, isomers can have different effects in biological systems: one isomer may have specific therapeutic activity while another isomer may have no therapeutic activity or may have entirely different forms of biological activity. Of the four isomers of ractopamine, it is known that RR-ractopamine is the most potent, both when tested in vitro (Mills et al., 2003a) and in vivo (Ricke et al., 1999); both publications are hereby included in their entirety by reference. Thus, when tested for binding affinity for porcine adrenergic β-2 receptors, RR-ractopamine was about 2.5 times as active as the mixture of all four isomers (Mills et al., 2003a.)

The HCl salt of the RR-isomer of ractopamine is called Butopamine Hydrochloride, USAN and has been tested as a cardiac stimulator for humans (Thompson et al., 1980), which publication is hereby included in its entirety by reference. Butopamine is considered to be a full agonist at the beta-2-receptor sites (Smith, 1998; Mills, 2002; Mills et al., 2003a, 2003b). which publications are hereby included in their entirety by reference.

The relative contributions of adrenergic beta-1- and beta-2-receptor activation to the pharmacological effects of ractopamine may also differ by the different ratio of the beta-receptor subtypes in tissues and species. Beta-1- and beta-2-receptor are co-expressed in most tissues, but the ratio of these receptor subtypes can vary such that beta-1-receptors are predominant in heart (70-80% in humans, 72% in pigs) and adipose tissue (75% in rats, 80% in pigs), while beta-2-receptors are predominant in skeletal muscle (60% in pigs), uterus (80% in humans) and lung (65% in pigs, 80% in humans or horses) (Ungemach, 2004, which publication is hereby includedin its entirety by reference.)

The development of RR-ractopamine (butopamine) was discontinued, reportedly due to cardiovascular side effects, such as for example severe tachycardia (Thompson et al., 1980). Cardiac side effects, such as tachycardia, are also seen with isoprenaline, which is also a full agonist on cardiac beta receptors. RR-ractopamine has been found also to be a full cardiac agonist on cardiac beta receptors, while SR-ractopamine is a partial agonist. Thus, RR/SR-ractopamine has partial agonistic activities. Full cardiac agonistic activity by an adrenergic beta-receptor agonist implies that said compound has adrenergic beta-receptor stimulating activity, while being devoid of adrenergic beta-receptor blocking activity. It is concluded that by using RR/SR-ractopamine instead of RR-ractopamine, the risk for cardiac side effects is decreased.

Adrenergic beta-receptor agonist drugs can have pharmacological and toxicological side effects that range from minor importance to major importance. Bronchial smooth muscle relaxation by adrenergic beta-2 stimulation may be a side effect of minor importance for healthy livestock animals. Ractopamine has been found to cause increased heart rate and CNS-mediated stress in livestock animals (Marchant-Forde et al., 2003, which publication is hereby included in its entirety by reference.) These are side effects of major importance, particularly since ractopamine is increasing the stress levels in animals—even during times with increased basal stress for the animals, such as during handling and (Marhant-Forde et al., 2003). Stress in swine, may induce the PSE syndrome in the animals, which means poor meat quality that is pale, soft and exudative, and becoming dry upon cooking.

As mentioned above, ractopamine is known to cause tachycardia in livestock animals, while R-salbutamol has the advantage of not causing tachycardia in the livestock animals. In the case of ractopamine, it has been suggested that the significant tachycardia in livestock animals may in part be caused by CNS-mediated stress (Marchant-Forde J. N., et al., 2003 and London C. J., et al, 2005, which publications are hereby included in their entirety by reference.) The combination of stress-induced tachycardia and beta-receptor mediated tachycardia is a serious side-effect of ractopamine and leads to cardiac tachyarrhythmias and increased lethality of livestock animals by sudden cardiac death (cardiac ventricular fibrillation.)

In many animals including livestock animals, stress manifests itself—directly or indirectly—in a range of forms extending from irritability to aggression. As pointed out above, stress may lead to cardiovascular side effects ranging from slightly elevated heart rate to serious tachycardia and cardiac arrhythmias, which in turn can lead to sudden death. The prevalence of stress-induced lethality varies among species; some having higher stress responsiveness than others (Odeh et al., 2003, which publication is hereby included in its entirety by reference.)

Stress in horses can be expressed in various ways, such as for example nervousness, anxiety and tachycardia and can be caused for example by heat, transportation and feed withdrawal. Stress in horses can also be induced by drugs or aggravated by drugs, such as for example adrenergic beta-receptor agonists that may be given to the horses of various reasons, such as for example as bronchodilators in heaves. CNS-mediated stress in horses may also lead to increased susceptibility for various diseases, such as for example allergic diseases or infectious diseases such as opportunistic bacterial infections. The use of an adrenergic beta-agonist that does not induce stress is particularly important in animals that are already suffering from stress or have a propensity for developing stress.

Stress in pigs is very common and some pigs have been shown to carry a specific stress-gene. Pigs that are homozygous to this gene are particularly stress-prone although heterozygous pigs are also more stress-prone than pigs that do not at all carry or express the stress-gene (Sterle, 2005, which publication is hereby included in its entirety by reference.) CNS-mediated stress in pigs can be expressed in various ways, such as for example aggression, tail-biting, and tachycardia and can be caused for example by heat, transportation, stocking density, human interventions, feed withdrawal, disease and aggression between males. Stress in pigs can also be caused or aggravated by drugs, such as for example ractopamine (Marchant-Forde et al. 2003.) Porcine Stress Syndrome (PSS) is triggered when pigs are subjected to stress associated with transportation, restraint, fighting, mating, exercise or hot and humid weather. Pigs with PSS become dyspneic, hyperthermic, cyanotic, develop muscle rigidity and such animals often die prematurely. Some degree of stress can be observed in most pigs and most pigs may therefore have propensity for stress. The administration of certain drugs, such as ractopamine to pigs may induce or aggravate PSS in swine. In addition to the well-known fact that stress induces increased mortality in swine, it has been demonstrated that stress has a negative effect on the quality of meat (Purdue; http://ag.ansc.purdue.edu/meat_quality/mqf_stress.html.) Thus, the muscles from stress-positive pigs often show the PSE syndrome (pale, soft and exudative). This condition causes the carcasses to be classified as being of unacceptable or inferior quality, since the meat from such animals tend to become dry when cooked, (Stadler K., which publication is hereby included in its entirety by reference.) The use of an adrenergic beta-agonist that does not cause stress is particularly important in animals that are already suffering from stress or have a propensity for developing stress.

Stress in ruminants can be expressed in various ways and in cattle ranging from anxiety to aggression or depression, increased body temperature and increased heart rate. Stress in cattle can be caused by a variety of factors, such as changes in environment, transportation, human contact, aggressive herd behaviour and changes in the herd social rankings, hunger, thirst, fatigue, injury or thermal extremes. The propensity for stress in cattle seems to affect most animals and the administration of drugs, such as ractopamine may induce or worsen CNS-mediated stress in cattle and particularly in cattle that are predisposed for stress. Stress in cattle is a serious condition and may lead to decreased quality of the meat and increased lethality among the animals. The use of an adrenergic beta-agonist that does not cause stress is particularly important in animals that are already suffering from stress or have a propensity for developing stress.

As other examples of ruminants, sheep also develop symptoms of CNS-mediated stress due to the same or similar factors as described above for other species and may include but are not limited to changes in the environment, transportation, human contact, aggressive herd behaviour, hunger, thirst, fatigue, injury or thermal extremes. The symptoms of CNS-mediated (psychological) stress are similar to those of other species and include anxiety, aggression, increased body temperature or increased heart rate. The consequences of stress are similar to those described above for other species and include risk for decreased quality of meat and sudden death of the animals. The administration of drugs, such as ractopamine, may induce stress in sheep or increase the symptoms of stress in said species. Stress in sheep can be a serious condition and may lead to decreased quality of the meat and increased lethality among the animals. The use of an adrenergic beta-agonist that does not cause stress is particularly important in animals that are already suffering from stress or have a propensity for developing stress.

As still another example, birds such as chickens, ducks, geese, turkeys, ostriches, emus or quails may also develop CNS-mediated stress by doses of ractopamine, corresponding to those necessary for obtaining increased muscle weight, decreased fat deposits and improved feed efficiency. Particularly, chickens in "grower houses" are suffering from stress or are predisposed to stress because of the high stocking density (up to 20,000 birds or more in very confined space). Symptoms of stress in birds, such as for example chickens, ducks, geese, turkeys, ostriches, emus and quails, can be expressed in various ways, as for example, anxiety, aggression, increased body temperature, tachycardia and lethality and can be caused for example by heat, transportation, high stocking density, sudden environmental factors, feed withdrawal, injury or disease. The administration of the beta-receptor agonist ractopamine may induce or increase stress in birds. CNS-mediated stress in birds—and particularly in chicken—may lead to decreased quality of the meat and increased lethality among the animals.

Stress may also manifest itself in farmed fish, such as for example barramundi, carp, cod, perch, salmon, trout and tilapia. Symptoms of stress and symptoms for predisposition (propensity) for stress in farmed fish can be observed as increased activity as for example during feeding frenzy and stress can lead to sudden death of the fish. Stress in fish can be caused for example by extreme temperatures, environmental factors, disease, parasites, handling or transportation. The administration of exogenous beta-receptor agonists may lead to stress in animals that are predisposed for developing stress or may cause a worsening of the symptoms of stress in fish, leading to decreased quality of the meat and increased lethality among the animals. The use of an adrenergic beta-agonist that does not cause stress is particularly important in animals that are already suffering from stress or have a propensity for developing stress.

Stress in dogs and in cats may be manifested by vocalization, changes in appetite, aggressive behaviour or otherwise changed attitudes or behaviours, or in other ways, such as described for other species above. The administration of drugs, such as ractopamine may induce stress in all dogs and cats and also in dogs and cats that are used as companion animals. Stress in dogs and cats may happen particularly in predisposed animals, such as for example in certain strains of dogs. Stress in dogs and cats can be a serious condition and may lead sickness and increased lethality. The use of an adrenergic beta-agonist that does not cause stress is particularly important in animals that are already suffering from stress or have a propensity for developing stress. Beta-receptor agonists, such as for example RR/SR-ractopamine may be used in dogs and cats that are over-weight or are in need of exercise. Due to their pharmacological effects, certain adrenergic beta-receptor agonists, such as for example RS- or R-salbutamol and RR/SR-ractopamine can also be used in animals that are compromised by various diseases, such as for example heart failure, where these drug may be used alone or in combination with diuretics or other drugs as known by those skilled in veterinary medicine.

Stress in animals can be monitored, judged and rated by individuals who are skilled in the art of animal psychology. In addition to monitoring and rating the behaviour of the animals, objective parameters are being used, such as for example determination of the concentration of circulating corticosteroid levels. (Post et al., 2003, which publication is hereby included in its entirety by reference.) Depending on the species, stress in animals in response to exogenous adrenergic stimulation can also be monitored by parameters such as body temperature, heart rate, spontaneous motility, aggression, ease of handling and even weight loss (Marchant-Forde et al, 2003.)

The use of an adrenergic beta-agonist that does not cause stress is particularly important in animals that are already suffering from stress or have a propensity for developing stress. As mentioned above, predisposition of stress in livestock animals is common and it will be advantageous to avoid the worsening of the stress in these animals that is induced by ractopamine. As pointed out below, stress has now been found not to be caused by RR/SR ractopamine, which makes this mixture of ractopamine isomers particularly useful in all the various animal species mentioned above.

SUMMARY OF THE INVENTION

We have previously reported that RR-ractopamine, when administered as an optically pure isomer dose not cause stress in animals (Aberg U.S. patent Ser. No. 11/755,378 (2007) and PPA 60/809,205 (2006), which documents are hereby included in their entirety by reference). It has now been found that RR-ractopamine is not chirally stable, but may epimerize over a short time-span of only days. The epimerization is facilitated by increased temperature and/or humidity. In contrast, RR/SR ractopamine is an isomerically stable mixture.

In studies of all four isomers of ractopamine and various combinations thereof, it has now surprisingly been found that the optical rotation at the "Me-site", but not the "OH-site" of the ractopamine molecule is of importance for the development of stress in animals. Thus, ractopamine isomers with S-configuration at the "Me-site" caused stress, while the same molecule with the corresponding R-configuration did not cause stress. Thus, neither RR-ractopamine nor SR-ractopamine caused stress in current laboratory tests.

It has also been found that contrary to RR-ractopamine, RR/SR-ractopamine is not a full agonist and RR/SR-ractopamine is therefore expected not to induce the cardiac side effects of full agonists, as described above.

Chemically, it has been found that the RR/SR-mixture of ractopamine can be obtained by extraction from ractopamine at reasonable cost and in manufacturing-scale batches, RR/SR-ractopamine can therefore be made at low cost. This is of particular importance for feed-additives in the extremely cost-sensitive livestock industry. As an example, in the broiler industry, the cost of the total dose of a growth-promoting agent given to each bird during the entire course of its lifespan, should preferably not be more than one U.S. cent per bird, most preferably not more than 0.8 U.S. cent per bird.

The present finding regarding the optical instability of ractopamine enantiomers is important since it particularly concerns RR-ractopamine. Thus, since RR-ractopamine is unstable at the "OH-site", it is forming SR-ractopamine by epimerisation thereby gradually decreasing in potency. An approximately 50/50 mixture of RR-ractopamine+SR-ractopamine, will herein also be called "RR/SR-ractopamine" or "SR/RR-ractopamine", or "racemic RR/SR-ractopamine" or "racemic SR/RR-ractopamine" or similar. The term "approximately", as used herein with reference to the concentrations of RR-ractopamine and SR-ractopamine in RR/SR-ractopamine refers, in the most preferred embodiment, to mixtures of RR-ractopamine and SR-ractopamine that may contain from 54 percent to 46 percent of RR-ractopamine together with 46 percent to 54 percent SR-ractopamine. Thus, in the most preferred embodiment, RR/SR-ractopamine may contain 54 percent RR-ractopamine in combination with 46 percent SR-ractopamine, or 46 percent RR-ractopamine in combination with 54 percent SR-ractopamine, or any combinations of RR-ractopamine and RS-ractopamine therein between.

In a less preferred embodiment, a mixture of RR-ractopamine and SR-ractopamine may contain from 79 percent to 21 percent of RR-ractopamine together with 21 percent to 79 percent SR-ractopamine.

Those skilled in the art of chemistry understand that chemical impurities, consisting of for example residual starting materials, extraction materials, solvents or RS-ractopamine or SS-ractopamine may appear in batches of RR/SR-ractopamine.

Parameters, such as for example the amount of adipose tissue ("fat") in an animal, the amount of muscle tissue ("lean meat") in an animal, growth of an animal, the feeding efficiency of an animal, and the muscle-to-fat ratio and the health of an animal can be greatly improved by administration of RR/SR-ractopamine, a pharmaceutically acceptable salt, solvate or polymorph thereof, while side effects such as aggressiveness and other symptoms of stress can be avoided or substantially avoided.

As pointed out above, said RR/SR-mixture of ractopamine is obtained by stereoselective extraction from RR/SS/RS/SR-ractopamine. Those skilled in the art of chiral chemistry know and understand that very small (less than 5 percent and often less than 2 percent) impurities of SS- and/or RS-ractopamine may be extremely difficult to avoid in batches of RR/SR-ractopamine. Such minimal impurities have negligible pharmacological effects and are therefore acceptable.

The administration of a therapeutically effective amount of RR/SR-ractopamine, pharmaceutically acceptable salts, solvates or polymorphs thereof, will maintain or improve the therapeutic effects of ractopamine, while side effects such as aggressiveness and other symptoms of stress that can be observed in animals given a formulation containing ractopamine can be avoided or substantially avoided by using said mixtures. The term "therapeutic effect" refers to increase in muscle mass (anabolic effect), decrease in fat deposits (lipolytic effects and inhibition of lipogenic activity), effect on muscle-to-fat ratio, and/or beneficial effects on feed efficiency. The term "substantially avoided" indicates that the side effects are minimized or completely eliminated, when administering RR/SR-ractopamine, a pharmaceutically acceptable salt, solvate or polymorph thereof at dosage rates at which commercially available ractopamine is customarily administered. Very high doses—such as doses used during toxicology testing—may cause death and may induce stress in addition to other side effects and toxic manifestations.

The pharmacological explanation(s) for the surprising finding that RR/SR-ractopamine does not cause stress in livestock animals is/are unknown, but the present finding is important since a major drawback with the administration of ractopamine is drug-induced stress with concomitant negative effects on the quality of the meat as well as the increased morbidity and mortality among animals treated with ractopamine, which side-effect can now be completely or substantially avoided by using RR/SR-ractopamine, which is a form of ractopamine that is economically feasible to manufacture.

Accordingly, the invention provides a method of promoting or improving the growth of muscle tissue and decreasing the lipids of fat cell and/or decreasing the number of fat cells of a subject by administering to said subject an effective amount of a mixture of SR-ractopamine and RR-ractopamine. Said subject can be an animal or a human. Weight-loss is obtained in said subject, particularly if said subject is overweight or obese. Stimulation of muscle growth may be of special importance when such stimulation is sought after, such as for example in subjects that of any reason have not been able to exercise, as for example may be the case in subjects that have undergone surgery and need rehabilitation.

It should be noted that the beneficial effects of adrenergic beta-receptor agonists on growth of muscle tissue and decrease of fat tissues is of relatively short duration in most animals, which is probably due to the down-regulation of adrenergic beta-receptors. In short, this means that the cells of the body—by unknown mechanisms—have the ability to protect themselves from adrenergic over-stimulation by decreasing the number of receptors available for stimulation by a beta-receptor agonist drug.

In particular, the present invention provides a method of promoting muscle growth, decreasing fat deposits or improving feed efficiency of animals, which comprises administering to said animal an effective amount of a mixture of the SR- and the RR-isomers of ractopamine.

Thus, in one embodiment, the present invention provides a method of promoting muscle growth (an anabolic effect) of an animal or a human by administering to said animal or human an effective amount of RR/SR-ractopamine.

In another embodiment, the present invention provides a method of promoting weight loss in animals and in humans, particularly in obese animals and obese humans, by mechanisms that are not fully understood, but that may include increased lipolytic activity and CNS-mediated decrease in appetite.

In another embodiment the invention provides a method of improving the muscle-to-fat ratio in an animal or a human by administering of RR/SR-ractopamine. Said improvement of the muscle-to-fat ratio is in part due to the anabolic activity described above and in part to the lipolytic activity and the lipogenic activity of RR/SR-ractopamine, but unknown mechanisms are believed to be involved as well.

In another embodiment, the present invention provides a method of improving the feed efficiency of an animal by administering to the animal an effective amount of a mixture of the SR-isomer and the RR-isomer of ractopamine.

In another embodiment, the present invention provides a method of improving muscle growth, decrease fat deposits, improve muscle-to-fat ratio, while avoiding polluting the environment with SS-ractopamine, RS-ractopamine or metabolites or break-down products thereof.

In another embodiment, the present invention provides a method of improving muscle growth, decrease fat deposits, improve muscle-to-fat ratio, while avoiding exposure of humans or animals to RS-ractopamine or SS-ractopamine or the metabolites thereof.

In still another embodiment, the tissue residues of total ractopamine are lower when RR/SR-ractopamine is being used as a growth promoter for livestock than when a mixture of all four isomers of ractopamine is being used. Thus, the present invention provides a method for decreasing tissue residues of ractopamine by administering to the animal a therapeutically effective amount of a ractopamine formulation that contains RR/SR-ractopamine. Therefore, humans eating the meat from livestock animals treated with RR/SR-ractopamine, rather than RR/SS/RS/SR-ractopamine, will be exposed to decreased amounts of total ractopamine. The term "total ractopamine" as used herein refers to the sum of all ractopamine isomers and metabolites thereof. The scientific explanation for the low tissue residues of total ractopamine in animals given a mixture of SR- and RR-ractopamine is not known, but it can be speculated that lower doses and an accelerated disposition of RR/SR-ractopamine as compared with RR/SS/RS/SR-ractopamine may contribute to favorably low tissue residues after administration of RR/SR-ractopamine.

In another embodiment, the invention provides a method of treating horses suffering from heaves by administering to these horses an effective amount of RR/SR-ractopamine or a formulation containing RR/SR-ractopamine. The administration of RR/SR-ractopamine to horses that are suffering from heaves induces effective broncho-relaxation, while avoiding excess cardiac stimulation. The therapeutic goals will be achieved without causing or worsening drug-induced CNS-mediated stress in these animals that often are significantly predisposed to stress because of their breathing difficulties.

In another embodiment the invention provides a protein-containing feed formulation including RR/SR-ractopamine. The feed formulation is capable of increasing lean meat deposition in an animal and/or improving the lean meat/fat ratio in an animal and/or promoting or improving the growth of an animal or improving the feed efficiency of an animal. The formulation contains a sufficient amount of a protein-containing animal feed mixed with RR/SR-ractopamine to provide from 1 to 500 ppm of RR/SR-ractopamine in the feed. The amount and concentration of crude protein and minerals in feed should be in excess of 13% and probably more than 17% (Adeola et al. 1990.) The feed efficiency will be more improved by adrenergic beta-agonists when the feed protein content is high and minimal levels are stated by law and varies between countries.

In still another embodiment the invention provides compositions and pharmaceutical formulations for use in the above methods, which include a therapeutically effective amount of RR/SR-ractopamine.

The use of the present invention will also facilitate the handling of animals, in particular livestock animals since animals treated with ractopamine are frequently demonstrating symptoms of stress and are therefore more difficult to handle than animals treated with RR/SR-ractopamine.

DETAILED DESCRIPTION

Those skilled in the art will appreciate that the invention described herein may be susceptible to variations and modifications other than those specifically described herein. The invention includes all such variation and modifications. The invention also includes all of the steps, features, formulations and compounds referred to or indicated in the specification, individually or collectively and any and all combinations or any two or more of the steps or features. Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by the specific embodiments described herein, which are intended for the purpose of exemplification only. Functionally equivalent products, formulations and methods are clearly within the scope of the invention as described herein.

The invention described herein includes a new method to make RR/SR-ractopamine from RR/SS/RS/SR-ractopamine. Those skilled in the art of chemistry will realize that modifications of the methodology described here may also lead to RR/SR-ractopamine. All such modifications are part of the present invention.

The invention described herein may include one or more ranges of values (e.g. dose, concentration, etc). A range of values will be understood to include all values within the range, including the values defining the range, and values adjacent to the range, which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The term "animal" includes animals of any species. The terms "individual" and "individuals" include humans and animals.

The terms "livestock" or "livestock animal(s)" as used herein refer to animals that are bred for human food, in particular farm animals such as ruminants (as for example cattle, goats and sheep), horses, swine, and deer, birds (such as for example chickens, turkeys, ducks, quails and geese), and farmed fish and farmed crustaceans.

The term "farmed fish" as used herein includes for example farmed barramundi, farmed carp, farmed cod, farmed perch, farmed salmon, farmed trout and farmed tilapia.

The terms "crustaceans" and "farmed crustaceans" as used herein refer to farmed crustaceans and farmed mollusks and includes for example farmed abalone, farmed freshwater crayfish, farmed blue mussel, farmed oyster, farmed prawns, farmed shrimp, farmed scallop, and farmed lobster.

The term "ractopamine" in this document refers to the free amine or to a salt or solvates of RR/SS/RS/SR-ractopamine. Thus, the term "ractopamine" refers to a mixture of approximately equal concentrations of the four enantiomers of ractopamine.

Terms like "SR-ractopamine", "pure SR-ractopamine", "pure SR-isomer of ractopamine" and the like, and "RR-ractopamine", "pure RR-ractopamine", "pure RR-isomer of ractopamine" and the like, and "RS-ractopamine", "pure RS-ractopamine", "pure RS-isomer of ractopamine" and the like and "SS-ractopamine", "pure. SS-ractopamine", "pure SS-isomer of ractopamine" and the like, refer to said isomer of ractopamine having an optical purity that is 95 percent by weight or better, which means that said isomer is present at a concentration of 95 percent by weight or more, while the total concentration (i.e. the sum) of the remaining isomers is 5 percent by weight or less, based on the total amount of ractopamine present. In a more preferred embodiment, the optical purity of said isomers is 98 percent or better and in the most preferred embodiment, the optical purity is 99 percent or better.

The terms "stress" and "CNS-mediated stress" are used as synonyms herein and refer to CNS-mediated (psychological) stress (as opposed to exercised-induced stress) with consequences leading to the expression of psychological or somatic symptoms such as for example aggressiveness, anxiety, depression, exhaustion, fatigue and/or other symptoms such as changes in body temperature, changes in the concentrations of circulating corticosteroids, increased heart rate, increased mortality and morbidity and decreased quality of meat products.

The term "growth promoter" as used herein, refers to a chemical entity that upon administration to livestock animals will have a favourable effect on feed efficiency and on the muscle-to-fat ratio in the carcass of said livestock animals. A growth promoter may, or may not, cause an increase in body weight.

The term "feed efficiency" as used herein, refers to the relationship between feed intake and muscle weight gain in livestock animals. Improved feed efficiency means that the ratio feed intake/muscle weight gain is decreased. Improved feed efficiency also means that the ratio muscle weight gain/feed intake is increased. The term feed efficiency may also refer to the feed intake/weight gain or weight gain/feed intake.

The term "muscle-to-fat ratio" as used herein, refers to the total weight of muscle (meat), divided with the total weight of body fat. The compounds of the present invention cause an increase in muscle weight and a decrease in total body fat, as described elsewhere in this document.

Other definitions for selected terms used herein will be found within the description of the invention and apply throughout. Unless otherwise defined, all other scientific and technical terms used herein have the same meaning as commonly understood by individuals who are skilled in the art to which the invention belongs.

Chemistry:

A synthetic method for making RR/SS/RS/SR-ractopamine was described by Anderson D. B. et al. (Eli Lilly): Growth Promotion. U.S. Pat. No. 4,992,473, which is hereby included in its entirety by reference.

Samples of ractopamine can be isolated and purified from conveniently available commercial sources. One kilogram of commercially available Paylean® (Elanco) was stirred overnight with 15 L of water. The mass was filtrated, and the filtrate (11.5 L) was evaporated under reduced pressure to a small volume (ca. 1-2 L). Aqueous potassium carbonate was added to raise pH to ca. 10, and the solution was extracted twice with equal volumes of ethyl acetate. The ethyl acetate extracts were combined, evaporated under reduced pressure to ca. 0.5 L, and an equal volume of hexanes added. After standing overnight, crystals of ractopamine free base (6.83 g) were filtrated. This material was crystallized again from ethyl acetate/hexanes to give pure ractopamine free base (6.01 g). HPLC showed 98.5% purity. A sample of ractopamine free base (120 mg) was stirred with 10 ml of deionized water cooled in an ice-water bath, and 2 M aqueous hydrochloric acid (2 ml) was added slowly. After stirring to dissolve the material, the solution was filtered and lyophilised to give ractopamine hydrochloride (125 mg). The mp was 128-135° C., lit (Merck Index) mp 124-129° C. $^1$H NMR was consistent. HPLC showed 98.0% chemical purity.

The single ractopamine isomers can be synthesized in laboratory scale according to the methodology of Ricke et al., 1999, which publication is hereby included in its entirety by reference. Methods for the preparation of single isomers of ractopamine have also been described by Mills J. et al. in Eur. Pat Appln. 7,205 and by Anderson D. B. et al. in U.S. Pat. No. 4,690,951, both of which are hereby incorporated in their entirety by reference. Additionally, a method for the preparation of RR-enantiomeric phenethanolamines was described by Anderson D. B. et al. in U.S. Pat. No. 5,643,967, which is hereby included in its entirety by reference.

Ractopamine has two chiral centers, and therefore four isomers exist (FIG. 1.) Commercially available ractopamine, is usually obtained by non-stereoselective synthesis, and consists of a mixture of almost equal amount of two diastereomeric racemates (ratio RR/SS to RS/SR=50:50). To our knowledge, no separation process is known that is aiming at obtaining RR/SR-ractopamine as the final product. Furthermore, to our knowledge, there is also no separation process reported to isolate the RR or the SR-ractopamine from the mixture of all four isomers, in a commercially useful way, e.g. by crystallization. Described here is a new separation process, based on crystallization and epimerization steps, useful in production scale and aimed at obtaining RR/SR-ractopamine as the final product.

In the new separation approach, first the two diastereomeric pairs (RR/SS and RS/SR) were separated from each other by formation of a salt with an achiral acid, preferably an aryloxacetic acid or an arylacetic acid, such as for example phenoxyacetic acid or naphthylacetic acid. The mixture of the four isomers of ractopamine free base was treated, for example with phenoxyacetic acid and the salt of RS/SR-ractopamine with phenoxyacetic acid was collected by filtration. The RS/SR-ractopamine acid addition salt can be purified by recrystallization to the desired level of diastereomeric purity. After purification by recrystallization and liberation of ractopamine from the ractopamine*acid salt by standard procedures, such as extraction under basic conditions, the pure racemic RS/SR-diastereoisomer of ractopamine was obtained.

This RS/SR-ractopamine racemate was resolved by formation of a complex with a chiral diamine, preferably enantiomerically pure 1,2-diaminocyclohexane or enantiomerically pure 1,2-diphenylethylenediamine. For example the RS/SR-ractopamine racemate was treated with (S,S)-1,2-diaminocyclohexane (S,S-DACH) to yield the SR-ractopamine*(S,S)-DACH complex. After recrystallization and complex splitting the pure SR-ractopamine was obtained. The terms "enantiomerically pure 1,2-diaminocyclohexane" and "enantiomerically pure 1,2-diphenylethylenediamine" refers to compounds having enantiomeric purity of 80% or better, preferably 90% or better and most preferably 95% or better. It is understood, that with a lower enantiomeric purity the process would also work, but the selectivity and therefote the yield would decrease.

It is also possible to isolate the SR-ractopamine*(S,S)-DACH complex directly from the mixture of all four isomers, but the selectivity and the overall yield proved to be significantly higher when first the two diastereomers were separated from each other.

The SR-ractopamine was epimerized, e.g. by heating with aqueous hydrochloric acid, to yield the desired mixture of RR- and SR-ractopamine. Under these conditions, one of the two stereocenters in ractopamine was epimerized to yield a 52:48 mixture of the two isomers RR and SR-ractopamine.

The RR/SS ractopamine diastereomers from the mother liquor of the first separation step can be epimerized, e.g. by heating in aqueous hydrochloric acid. Said epimerization regenerated the original mixture of all four isomers. This mixture is reused in the separation process, thereby significantly increasing the total yield of the present method. Also, the ractopamine material dissolved in the mother liquors from the recrystallization steps can be reused in the process, after isolation or directly, which will further increase the overall yield. The chiral complex builder, e.g. DACH or 1,2-diphenylethylenediamine, used in the resolution step can be isolated and reused in the process, as known to those skilled in the art of chemistry.

Those skilled in chemistry realize that also R,R-DACH can be used in the resolution step. In this case, the desired enantiomer would be obtainable from the mother liquor of the resolution step.

Those skilled in chemistry also realize that RR/SR-ractopamine can be obtained by epimerisation of RR-ractopamine as described above for SR-ractopamine.

With the right combination of the reported steps (separation of diastereomers with an achiral acid, e.g. phenoxyacetic acid, resolution of the RS and the SR-enantiomers with enantiopure DACH and selective epimerization of one stereocenter) all enantiomers of ractopamine, especially the SR and the RR enantiomers, are obtainable in a pure form starting from the commercially available mixture of the four isomers.

The RR enantiomer is also obtainable by the separation of the RR/RS ractopamine diastereomers by crystallization of an acid addition salt with an achiral acid, as described above for the separation of the RR/SS and RS/SR-ractopamine diastereomers.

The RR enantiomer could be also obtained by resolution of the racemic RR/SS-ractopamine mixture, e.g. by formation of a complex with a chiral complex builder, like a chiral amine. The required racemic RR/SS-ractopamine mixture itself is obtainable from the RR/SS/RS/SR-ractopamine mixture by crystallization of an acid addition salt with an achiral acid, as described above. RR-ractopamine can be epimerised, as described for SR-ractopamine, to obtain RR/SR-ractopamine.

Experimental
1. Making RR/SS/RS/SR-Ractopamine Free Base

RR,SS,RS,SR-ractopamine hydrochloride (6925 g; 20.5 mol) was dissolved in 69.25 kg of water under stirring at 45-50° C. To the cooled solution (0-5° C.) were added 4.1 kg of 20% aqueous sodium hydroxide (820 g, 20.5 mol) and the reaction mixture was stirred for 30 min at room temperature. The obtained RR,SS,RS,SR-ractopamine free base precipitation was filtered off, washed with water and dried.

2. Making RS/SR Ractopamine*Phenoxyacetic Acid

To a solution of RR,SS,RS,SR-ractopamine free base (6178 g; 20.5 mol) in 35 kg of isobutanol was added phenoxyacetic acid (3119 g, 20.5 mol) and the mixture was stirred at room temperature over night. The obtained white precipitate was filtered off, washed with isobutanol (3×900 ml) and tert.-butylmethylether (TBME) (3×500 ml) and dried on air. RS/SR-ractopamin*phenoxyacetic acid was isolated as a white powder. Yield: 5900 g (13 mol) (diastereomeric ratio (D.R.): RS/SR-71%; RR/SS-29%)

3. Purifying RS/SR Ractopamine*Phenoxyacetic Acid

A mixture of RS/SR-ractopamine*phenoxyacetic acid (5900 g; 13 mol; d.r.: RS/SR-71%; RR/SS-29%) and 5250 g of methanol was stirred at 55° C. for 1 hour and then at room temperature over night. The obtained precipitate was filtered off, washed with TBME (2×250 ml) and dried on air. RS/SR-ractopamin*phenoxyacetic acid (4000 g) was isolated as a white powder.

This RS/SR-ractopamine*phenoxyacetic acid (4000 g, 8.82 mol) was suspended in 3000 g of methanol and stirred at 55° C. for 1 hour, then at room temperature over night. The precipitate was filtered off, washed with TBME (2×600 ml) and dried on air to yield RS/SR-ractopamin*phenoxyacetic acid as a white powder (3650 g) (DR: RS/SR-100%; RR/SS-0%).

4. Making RS/SR-Ractopamine

To RS/SR-ractopamin*phenoxyacetic acid (3580 g; 7.89 mol) in 3580 g of water was added 37% hydrochloric acid (934 g; 9.47 mol) and the mixture was stirred at room temperature for 30 min.

Then 17.9 kg of TBME were added and the mixture was stirred at room temperature for 30 min. The organic phase was separated. To the water layer was added 1895 g of a 20% NaOH solution (379 g; 9.47 mol) and the formed suspension was stirred for 15 min. The water was decanted. The remaining viscous residue was dissolved in 17.5 kg of methanol and the resulting solution was evaporated to dryness to obtain RS/SR ractopamine (2240 g; 94%).

5. RS/SR-Ractopamine Resolution with S,S-Diaminocyclohexane (S,S-DACH)

To a solution of RS/SR-ractopamine (186.58 g; 0.619 mol) in 653 g of tetrahydrofuran (THF) was added S,S-DACH (70.69 g; 0.619 mol) and the mixture was stirred at room temperature over night. An obtained precipitate was collected by filtration, washed with THF (50 ml), TBME (2×70 ml) and dried to yield SR-ractopamine*S,S-DACH (122.11 g; 0.294 mol).

This obtained SR-ractopamine*S,S-DACH (122.11 g; 0.294 mol) was dissolved in 610 g of THF and stirred at 55° C. for 1 hour. Then the solution was cooled to room temperature and stirred for further 20 hours. The obtained crystals were filtered off and dried to yield SR-ractopamine*S,S-DACH (83.65 g; 0.201 mol) (ER: SR-97.3%; RS-2.7%).

6. Making SR-Ractopamine

To a solution of S,R-ractopamine*S,S-DACH (83.65 g, 0.201 mol) in 1255 g of methanol was added a solution of D-tartaric acid (30.21 g 0.201 mol) in 302 g of methanol and the mixture was stirred at room temperature for 2 hours. The precipitate was filtered off and washed with 60 ml of methanol.

The combined filtrate was evaporated to dryness to yield S,R-Ractopamine (57.8 g; 95%).

7. Making RR/SR-Ractopamine HCl by Epimerization of SR-Ractopamine

To 54.2 g (0.180 mol) of SR-ractopamine in 360 ml of water were added 360 ml of 2N hydrochloric acid and the reaction mixture was stirred under argon at 70-75° C. for 1 hour and then at 5° C. over night. The solvent was evaporated under reduced pressure, the obtained residue was co-evaporated with toluene (2×100 ml). The obtained solid was dried in vacuum to yield 53.88 g (89%) of RR/SR Ractopamine hydrochloride (D.R.: SR-49%; RR-50%).

8. Epimerization of RR/SS Ractopamine

To RR/SS-ractopamine (775 g; D.R.: RR/SS-89%; RS/SR-11%), isolated from the mother liquor of experiment-2, was added 2 kg of water and 991 g of concentrated hydrochloric acid and the reaction mixture was stirred at 70-75° C. for 2 hours and then at 22° C. over night. Then, a 20% solution of NaOH (2010 g) was added and the mixture was stirred for 15 min. The water was decanted from the obtained precipitate. The residue was dissolved in methanol (2.3 kg) and the obtained solution was concentrated under reduced pressure to yield quantitatively RR/SS/RS/SR-ractopamine (D.R.: RR/SS-51%; RS/SR-49%).

9. RS/SR/RR/SS-Ractopamine Resolution with S,S-Diaminocyclohexane

To RS/SR/RR/SS-ractopamine (396.4 mg; 1.32 mmol) in 1 ml of THF was added S,S-DACH (75 mg; 0.66 mmol) and the reaction mixture was stirred for 7 hours at room temperature. The obtained precipitate was collected by filtration, washed with TBME (2×0.5 ml) and dried to yield the SR-ractopamine*S,S-DACH: 81.5 mg (e.r.: RS-23.3% SR-76.7%)

10. Separation of RR/SR-Ractopamine with 1-Naphthylacetic Acid

RR/SR-Ractopamine (49 g; 163 mmol) was dissolved in 225 g of isobutanol and 2.2 g of water at 50° C. To the solution was added 1-Naphthylacetic acid (30.28 g, 163 mmol) under stirring. The mixture was homogenized at 50° C. and then stirred at 8° C. for 64 hours. An obtained white precipitate was filtered off, washed with TBME (2×30 ml) and dried on air to yield RR/SR-Ractopamine*1-Naphthylacetic acid (18.2 g; dr: RR-77.8%; SR-22.2%) as a white powder. To this RR/SR-Ractopamine*1-Naphthylacetic acid (18.20 g; 37 mmol; dr: RR-77.8%; SR-22.2%) were added 72.8 g of ethanol and stirred at 50° C. for 1 hour, then at room temperature over night. The precipitate was filtered off, washed with ethanol (9 ml), TBME (2×15 ml) and dried on air. This procedure was repeated twice to yield RR-Ractopamine*1-Naphthylacetic acid (11.83 g; dr: RR-97%; SR-3%) as a white powder. To this RR-Ractopaminen-Naphthylacetic acid (8.9 g; 18 mmol; dr: 97:3) in 89 g of water was added 2N Hydrochloric acid (11 ml; 22 mmol) and stirred at room temperature for 10 min. 1-Naphthylacetic acid was removed by extracting with TBME (2×55 ml). To the aqueous solution was added 1N NaOH (22 ml; 22 mmol) and stirred for 10 min. RR-Ractopamine was extracted with isopropylacetate (3×90 ml) and dried over Na$_2$SO$_4$. The solvent was evaporated and the obtained RR-Ractopamine was dried in vacuum to yield 5.14 g (dr: RR-97.6%; SR-2.4%)

The present invention relates to a method of administering to animals a therapeutically effective amount of RR/SR-ractopamine, whereby an increase in muscle mass, a decrease in body fat deposits and improvement of feed efficiency are obtained in livestock animals, while alleviating the concomitant liability of certain adverse side effects associated with the administration of RR/SS/RS/SR-ractopamine. It is understood by those skilled in the art that increased total body weight occurs when the increase in muscle weight exceeds the loss in weight caused by the loss of fat tissue.

Decreased morbidity and mortality is expected to be achieved in livestock animals treated according to the present invention. There are financial advantages for livestock breeders to use the present invention, particularly since the cost of manufacturing RR/SR-ractopamine is lower than the manufacturing cost for any single isomer of ractopamine. In addition, an improvement of lean-ness is obtained, which gives higher financial returns to the breeders.

The present invention also relates to a method of decreasing residues of ractopamine in the carcasses of animals. To this end, administration to livestock animals of therapeutically effective amounts of RR/SR-ractopamine or of a formulation containing RR/SR-ractopamine, rather than ractopamine, decreases of the residual concentrations of total ractopamine in various parts of the carcass are obtained. Thus, the exposure of humans eating meat from livestock animals treated with RR/SR-ractopamine will be less exposed to drug residues than would be the case if RR/SS/RS/SR-ractopamine had been used as a repartitioning agent.

The terms "ractopamine" or "isomer" or "mixture" as used herein refer not only to the free base, but also refer to acid addition salts or solvates thereof. Acid addition salts include, for example addition salts prepared with various acids, for example, hydrochloric acid, hydrobromic acid, sulphuric acid, phosphoric acid, nitric acid, or organic acids, such as citric acid, fumaric acid, tartaric acid, acetic acid, maleic acid, benzoic acid, p-toluenesulphonic acid, methanesulphonic acid, and the like. Hydrate forms and polymorphs are also included in the present invention; particularly forms that can be manufactured as dry powder or forms that are water-soluble. Reference is made to Merck Index 11th edition (1989) items 9089, 209, 3927, 4628, 8223, 5053, 5836, 8142, 2347, 7765, 1840, 9720, 7461, 1317, 4159, and 963 and references cited therein and, to Am. Rev. Resp. Dis. 1988, 137: (4; 2/2) 32, the disclosures of which are herein incorporated in their entirety by reference. Importantly, the free amine form of pure, or substantially pure RR/SR-ractopamine, has now been found to be optically stable, which is contrary to single isomers, such as RR-ractopamine or SR-ractopamine.

Like other adrenergic beta-receptor agonists (WO 2006/064283 A1; included hereby in its entirety by reference), ractopamine, RR/SR-ractopamine, mixtures of ractopamine isomers and single isomers of ractopamine are expected to have various polymorphs, some of which are expected to have favourable physicochemical properties, favourable crystalline structure and/or favourable chiral stability and/or favourable biological effects. All such polymorphs are expected to be found and are hereby encompassed in the present invention.

Long-term stability testing of mixtures of SR- and RR-ractopamine, including RR/SR-ractopamine has not been concluded and it is possible and may be expected that the free amine or some of the salt form(s) may be more optically and/or chemically stable than the hydrochloride salt. The free amine SR-ractopamine has the chemical name SR-4-hydroxy-a-[[[3-(4-hydroxyphenyl)-1-methylpropyl]amino] methyl]benzene methanol. RR-ractopamine hydrochloride has the chemical name RR-4-hydroxy-a-[[[3-(4-hydroxyphenyl)-1-methylpropyl]amino]methyl]benzene methanol HCl; melting point 176-176.5°; optical rotation [alpha]$_D$-22.7°; [alpha]$_{365}$-71.2° (c=3.7 mg/ml in methanol) (Merck Index, 1996, 12: 1392-1393, hereby included in its entirety by reference).

As used herein, the terms "therapeutically effective amount" or "effective amount" or the like refer to an amount of compound, such as for example an adrenergic receptor agonist, that is sufficient to obtain a sufficient, sought-after, expected or wanted beneficial effect. In the present context and with regard to animals, a sufficient beneficial effect is considered to be present, if one or more of the aforementioned effects are achieved. In particular, a sufficient beneficial effect is considered to be present, if the treatment offers a financial return of at least the cost of the treatment, more preferably at least three times the cost of the treatment. The financial returns of the treatment may vary among animal species and will depend on factors like decreased mortality, decreased morbidity, improved meat quality, cost of treatment, improved lean/fat pricing bonus, etc. As will be realized by those skilled in the art, the amount of RR/SR-ractopamine constituting such an amount of drug will depend on the animal species, the duration of the treatment and numerous other factors, as for example weight of animals, age of animals, species and subspecies of animal, etc.

The administration of ractopamine is known to induce stress in livestock animals and can also cause worsening of existing stress in said animals. The methods of the present invention are particularly useful for treating livestock animals with a growth promoter, a repartitioning agent, etc., if said animals already suffer from stress that is induced by their environment or by other factors, since drug-induced stress by adrenergic beta-receptor agonists, such as ractopamine may significantly add to, potentiate, or make worse existing stress in the animals.

Repartitioning includes a decrease in fat combined with an increase in muscle cells. The decrease in fat is mainly achieved by adrenergic beta-receptor mediated lipolysis. The combination of the RR- and the SR-enantiomers in RR/SR-ractopamine is expected to be a very potent repartitioning agent since practically all of the lipolytic activity of RR/SS/RS/SR-ractopamine resides in the RR and the SR enantiomers (Mills et al 2003a, FIG. 4). As well known to those skilled in the art of pharmacology, activation of adrenergic beta-receptors leads to increased intracellular adenylcyclase activity and it has been reported (Mills et al. 2003a, FIG. 3) that only the RR- and the SR-enantiomers significantly ($P<0.05$) increased adenyl cyclase activity through porcine beta-2 receptors, while the SS- and the RS-enantiomers had no or almost no functional effect. Thus, although the RS-enantiomer of ractopamine has higher affinity for the adrenergic beta-2 receptor than the SR-enantiomer, the functional activities of the SR-enantiomer supersede those of the RS-enantiomer. Since RS-ractopamine has affinity for the beta-2 receptor, without causing adenylcyclase activation and without causing any lipolytic effects, it is possible that this enantiomer has adrenergic beta-2 receptor inhibitory activity, which may compromise the effectiveness of the RR- and the SR-enantiomers in a mixture of all enantiomers. The SS-isomer does not have affinity for the receptor, does not activate adenylcyclase and is considered to be therapeutically inert. An absence of therapeutical activity does not mean that a compound is devoid of pharmacological side effects or toxic effects and it is believed that both the RS- and the SS-isomers carry unwanted biological activities. Thus, the combination of RR- and SR-ractopamine is more potent as a repartitioning agent than the RR/SS/RS/SR-mixture of all four enantiomers and is well positioned to improve the quality of the carcasses of livestock animals. The term "improve the quality of the carcass" as used herein implies an increase in lean muscle weight, decrease in fat content, increase of the lean/fat ratio and avoidance of impaired meat quality, such as for example dry meat, discolored meat and PSE syndrome meat.

It has now surprisingly been found that treatment of animals with RR/SR-ractopamine, does not cause stress in said animals. This does not mean that RR/SR-ractopamine should be expected to cure stress, but administration of the repartitioning agent RR/SR-ractopamine is expected not to worsen existing stress or induce additional stress in animals, which is of particular importance in animals and particularly in livestock animals that are predisposed or prone to stress. Livestock animals may be predisposed to stress due to environmental factors, such as diseases, hereditary factors, feeding frenzy, animal density with large numbers of animals in small spaces, etc.

The use of RR/SR-ractopamine rather than RR/SS/SR/RS-ractopamine will completely eliminate or substantially reduce toxic effects and pharmacological side effects that reside in the RS- or SS-isomers of ractopamine. The use of RR/SR-ractopamine rather than RR/SS/SR/RS-ractopamine will completely eliminate toxic effects and pharmacological side effects that reside exclusively in the RS- or SS-isomer of ractopamine.

The use of RR/SR-ractopamine in livestock species minimizes or eliminates any side effect that is the result of interaction by the distomeric RS- or SS-isomers of ractopamine with beta-receptor activities, absorption, distribution, metabolism and excretion of the eutomeric RR- and SR-isomers of ractopamine.

The use of RR/SR-ractopamine, rather than RR/SS/RS/SR-ractopamine, as a growth promoter in livestock animals will decrease the tissue drug residues of total ractopamine in the edible parts of livestock animal bodies since RR/SR-ractopamine is more potent as a beta-receptor agonist than RR/SS/RS/SR-ractopamine and RR/SR-ractopamine can therefore be used in lower doses than RR/SS/RS/ST-ractopamine. The use of RR/SR-ractopamine may eliminate drug residues of the other isomers. The use of the two isomers SR-ractopamine and RR-ractopamine rather than a mixture of all four isomers may also have advantages at sites of metabolism and at the receptor sites, since drug interactions, beta-receptor antagonistic activity and beta-receptor down-regulation by the other isomers can be avoided or reduced.

It has repeatedly been demonstrated that a distomeric beta-receptor agonist may have unwanted side effects, such as pro-inflammatory activity and bronchial pro-constrictor activities (Agraval et al. 2004; Baramki et al, 2002). The use of the eutomeric mixture RR/SR-ractopamine may therefore offer beneficial advantages since any pro-inflammatory effects of the distomeric isomers, i.e. SS- and RS-isomer, and any smooth muscle hyperactivity or hyper-reactivity that may be induced by said distomeric molecules will be completely or substantially avoided. The avoidance of any bronchial-contracting side effects of RS- and SS-ractopamine are of particular importance when RR/SR-ractopamine is used as medication for horses, suffering from heaves and the avoidance of pro-inflammatory effects are of importance when RR/SR-ractopamine is used as weight-loss medication for animals and humans in need thereof, such as for example obese companion animals and obese humans.

RR/SR-ractopamine also offers beneficial cardiac effects and this form of ractopamine has not revealed detrimental effects on cardiovascular parameters at concentrations or doses that correspond to the therapeutic doses, which, for example are the doses of RR/SR-ractopamine that are suitable for growth promotion in livestock animals, the treatment of heaves in horses or the treatment of obesity in companion animals and humans.

The development of the full agonist RR-ractopamine as a cardiovascular and/or cardiac drug for humans was discontinued due to side effects of said enantiomer, such as excessive tachycardia. RR/SR-ractopamine is a partial agonist and may therefore be used as cardiac medication for humans and animals in need thereof, such as for example in companion animals that are suffering from heart failure. The risk for cardiac side effects by RR/SR-ractopamine is less than such risks by the single RR-ractopamine enantiomer.

For breeders of livestock animals, the method of the present invention yields leaner animals, which command higher prices from the meat industry. It was also noted that feed efficiency and/or animal muscle growth rate are significantly enhanced when the methods of the present invention are followed.

In one embodiment, the invention offers a method of improving or promoting the growth of an animal by administering to the animal a therapeutically effective amount of RR/SR-ractopamine. When RR/SR-ractopamine is used as a growth promoter for livestock, it is possible to reduce the dose from the doses used for RR/SS/RS/SR-ractopamine, thereby lowering costs of handling and transports of the less bulky material.

When using ractopamine in animals, the environmental impact will be reduced by using RR/SR-ractopamine rather than the RR/SS/RS/SR-mixture of ractopamine, since neither of the RS- or SS-isomers or the metabolites thereof will pollute the environment.

It may be particularly beneficial to eliminate the administration of the distomeric RS- and SS-isomers of ractopamine to animals since the distomeric isomers may cause side-effects both in the livestock animals and in humans eating such animals, particularly since at least the SS-isomers is completely devoid of adrenergic beta-receptor stimulating activity and the RS-enantiomer has reduced beta-receptor activity as described by Shappell et al, 2000, which publication is hereby included in its entirety by reference.

Furthermore, although there may be variability in therapeutic response from one species to another, from one subspecies to another and from one animal to another by administering RR/SR-ractopamine, it is possible to accomplish a more targeted treatment of the animals. In particular, this is important since it is not desirable to administer to animals, and particularly not to livestock animals, a compound with a multifaceted spectrum of pharmacological activities, pharmacological side effects and toxic effects. The term "a more targeted treatment" in this context means that by using RR/SR-ractopamine, the focused therapeutic activity of said isomers can be taken advantage of without also having unwanted consequences of the RS- or SS-isomers.

In one embodiment, the present invention provides a method of improving the feed efficiency of an animal by administering to the animal a therapeutically effective amount of RR/SR-ractopamine devoid or substantially devoid of the RS- and SS-isomers of ractopamine. More particularly, the ractopamine preparation used in this form of the invention contains a mixture of the pure or substantially pure forms of the RR- and SR-isomers of ractopamine.

In another embodiment, the invention provides a method of improving the muscle to fat ratio in an animal by administering to the animal a therapeutically effective amount of RR/SR-ractopamine that is devoid or substantially devoid of the RS- and the SS-isomers of ractopamine. More particularly, the ractopamine preparation used in this form of the invention contains a mixture of the pure or substantially pure forms of the RR- and SR-isomers of ractopamine.

In another embodiment, the present invention provides a method to improve the financial returns for livestock producers, since low-fat carcasses attract a premium price that may be higher than 30 percent (International Egg and Poultry Revue, USDA, Aug. 2, 2005. www.ams.usda.gov/poultry/mncs/International. PoutlryandEgg/2005Reports/x080205.pdf, which publication is hereby included in its entirety by reference.)

The use of RR/SR-ractopamine in livestock species minimizes or eliminates any side effect that is the result of interaction by the distomeric RS- or SS-isomers of ractopamine with the efficacy, absorption, distribution, metabolism and excretion of the eutomeric RR- and SR-isomers of ractopamine.

Use of the methods of the present invention provides a means for improving the quality of meat from livestock animals by reducing stress and factors leading to stress, said stress being known to decrease the quality of meat (Sterle, 2005, which publication is hereby included in its entirety by reference).

Use of the methods of the present invention also provides a means of preventing or reducing morbidity, particularly attributable to stress, stress during transportation, aggressive interactions between animals and cardiovascular or respiratory events caused directly or indirectly as a consequence of the administration of RR/SS/RS/SR-ractopamine to the animals.

Use of the methods of the present invention also provides a means of preventing or reducing smooth muscle hyperactivity or hyperreactivity, as well as pro-inflammatory effects in mammals, caused directly or indirectly as a consequence of the administration of the RS- or the SS-isomers of ractopamine to the mammal.

The environmental impact of dosing livestock animals with RR/SR-ractopamine rather than ractopamine will be significant since neither the RS- nor the SS-isomers of ractopamine nor the metabolites thereof will pollute the environment. Additionally, a favourable environmental impact will also come from the fact that the doses of RR/SR-ractopamine by weight will be lower than the corresponding doses of RR/SS/RS/SR-ractopamine.

The present invention also relates to food compositions including an admixture of food materials containing RR/SR-ractopamine. Said mixture is preferentially administered in the feed to animals that are being given a diet, consisting of protein-containing food materials. Accordingly, in another embodiment, the invention provides a protein-containing animal feed preparation, to which has been added RR/SR-ractopamine, said admixture being capable of increasing lean meat (muscle) content in an animal and/or improving the muscle-to-fat ratio in an animal and/or improving the growth of an animal and/or improving the feed efficiency of an animal, while avoiding certain side effects, such as for example stress. The amount of RR/SR-ractopamine will be generally chosen to provide from a total of about 1 to about 500 ppm of said admixture of RR/SR-ractopamine in said food material. The term "ppm" refers to parts per million, more specifically to "gram per ton" and 10 ppm equals 10 gram of RR/SR-ractopamine per metric ton of food material.

The daily dose of RR/SR-ractopamine to animals varies widely and depends on the animal species, the size of the animal, the route of administration and the effect(s) sought. In general, the daily doses of RR/SR-ractopamine to animals varies between 0.01 mg to 500 mg per day, of which the lowest doses are intended for small animals and the highest doses are intended for large mammals.

For distribution purposes an admixture of a high concentration of RR/SR-ractopamine is prepared in a suitable premix. Said premix may contain 1 to 10% of RR/SR-ractopamine in diluents (usually feed, which may be reinforced with additional proteins) and may also contain other active ingredients, such as antibiotics and/or immunostimulating compound(s). The premix is distributed to the end users in bags containing said premix. The end-user, usually the farmer/breeder raising the livestock animals, will further dilute the premix into the regular protein-containing feed that is used for said livestock animals. Accordingly, in another embodiment the invention provides a premix formulation, which is an animal feed preparation containing the admixture of RR/SR-ractopamine in diluents for distribution purposes. Diluents suitable for use to make up the feed supplement compositions may include the following: alfalfa meal, soybean meal, cottonseed oil meal, linseed oil meal, sodium chloride, cornmeal, cane molasses, urea, bone meal, corncob meal, rice kernel and the like. The premix promotes a uniform distribution of the active ingredients in the finished feed into which the premix is blended. It thus performs an important function by ensuring proper distribution of the active ingredient throughout the feed. If the premix admixture is used as a top dressing for feed, the premix likewise helps to ensure uniformity of distribution of the active material across the top of the dressed feed.

Since RR/SR-ractopamine is chemically stable in water, the premix may consist of water or may contain water. Thus, if the intention is to supply animals with drinking water that is supplemented with RR/SR-ractopamine, a premix can be prepared, containing a fixed concentration of RR/SS-ractopamine in a dry, water-soluble carrier or in a suitable volume of a fluid, such as water, which, in turn, can be added to the drinking water of the animals, by adding said premix volume directly to the drinking water of the animal or by adding said premix to an automatic drinking system for animals.

Of importance is that the feed to the animal contain proteins, the presence of which in feed is a well-known prerequisite for muscle growth in all species. The dietary protein requirements for various livestock species are well known for those skilled in the art. As an example, a maize-soybean meal diet, can be used for broiler chicken, wherein the crude protein concentration should preferably not be less than 17 percent by weight of the feed.

The preferred medicated swine feed generally contain from 1 to 200 grams of RR/SR-ractopamine per metric ton of feed, the optimum amount for these animals usually being from 1 to 100 grams per ton of feed.

The preferred medicated drinking water for swine will generally contain from 1 to 200 ppm by weight of RR/SR-ractopamine.

The preferred medicated feed for ruminants, such as for example cattle, goats and sheep, generally contains from 5 to 500 grams of RR/SR-ractopamine per ton of feed, the optimum amount for these animals usually being about 10 to 200 grams per ton of feed.

The preferred medicated drinking water for cattle, goats and sheep, generally contain 5 to 500 ppm by weight of RR/SR-ractopamine.

The preferred medicated feed for chicken and turkeys generally contains from 1 to 100 grams of RR/SR-ractopamine per ton of feed, the optimum amount for these animals usually being about 2 to 50 grams per ton of feed.

The preferred medicated drinking water for birds, such as for example chicken and turkeys, generally contain 1 to 50 ppm by weight of RR/SR-ractopamine.

The preferred medicated feed for dogs and cats generally contains from 1 to 100 grams of RR/SR-ractopamine per ton of feed, the optimum amount for these species usually being 2 to 50 grams per ton of feed.

The preferred medicated drinking water for dogs and cats generally contain 1 to 100 ppm of RR/SR-ractopamine by weight.

In summary, when administered in the feed to swine, the concentration of RR/SR-ractopamine will be 1 to 200 ppm; when administered in the feed to ruminants, the concentration will be 5 to 500 ppm; when administered in the feed to birds, the concentration of RR/SR-ractopamine will be 1 to 100 ppm; when administered to cats and dogs in the feed, the concentration of RR/SR-ractopamine will be 1 to 100 ppm. Thus, when administered to animals in the feed, the concentration range is 1 to 500 ppm of RR/SR-ractopamine.

In summary, when administered in the drinking water to swine, the concentration of RR/SR-ractopamine will be 1 to 200 ppm; when administered in the drinking water to ruminants, the concentration will be 5 to 500 ppm; when administered to birds, the concentration of RR/SR-ractopamine in the drinking water will be 1 to 50 ppm; when administered to cats and dogs in the drinking water, the concentration of RR/SR-ractopamine will be 1 to 100 ppm. Thus, when administered to animals in the drinking water, the concentration range is 1 to 500 ppm of RR/SR-ractopamine.

The magnitude of a therapeutic dose of RR/SR-ractopamine to horses in the management of heaves will vary with the severity of the disease to be treated, and other conditions, such as for example the size of the animal. The dose of RR/SR-ractopamine used to treat horses with heaves will offer an amount sufficient to alleviate bronchospasms but insufficient to cause adverse effects. The dose needed to obtain an optimal therapeutic effect will vary and will depend on the route of administration, the dosing frequency and will also vary according to the age, body weight, and response of the individual horse. In general, the total daily dose ranges when administered by inhalation, for the conditions described herein, is from about 0.1 microgram to about 1000 micrograms per kilogram bodyweight two or four times daily. Any type of inhaler for horses may be used. Preferably, a daily oral dose range should be between about 0.2 milligrams to 200 milligrams, two to four times daily; all doses will have to be titrated according to the severity of the symptoms as well known by the caring veterinary staff. A controlled-release tablet may be more convenient than an instant-release tablet and may contain at least twice the amount of RR/SR-ractopamine as an instant release tablet or for example between 4 and 400 mg RR/SR-ractopamine. Part of the dose of RR/SR-ractopamine in a controlled-release tablet may be contained in the coating of the tablet for immediate release and the remaining dose of RR/SR-ractopamine may be contained in the core of the tablet for controlled release later. Controlled-release tablets may be given to the horse once or twice daily, while instant-release tablets may have to be given to the horse up to 4 times daily. In managing the horse suffering from heaves or from another bronchial ailment that includes bronchial smooth muscle constriction, hyperreactivity or hyperactivity, the therapy should be initiated at a lower dose, perhaps about twice daily dosing with 1 milligrams to about 12 milligrams and increased up to about twice daily dosage of 10 milligrams or higher depending on the horse's global response. It is further recommended that older horses and horses with impaired renal, or hepatic function, initially receive low doses, and that they be titrated based on individual response(s) and blood level(s). It may be necessary to use dosages outside these ranges as will be apparent to those skilled in the art. Further, it is noted that the treating veterinarian would know how and when to interrupt, adjust, or terminate therapy in conjunction with the individual horse's response. Analogous dosages and dosage forms apply to other animal species that may be administered RR/SR-ractopamine to induce relief from bronchoconstriction.

In a particular embodiment of the methods of the invention, pure or substantially pure RR/SR-ractopamine is administered in combination with at least one antibacterial agent. The term "antibacterial agent(s)" or "antibacterial compound(s)" or the like, as used herein, comprises various types of compounds and feed additives, such as compounds having bactericidal effects or bacteriostatic effects and compounds that in other ways protect from infections, such as for example immunostimulating compounds. Examples of immunostimulating compounds are for example beta glucans, such as for example beta 1.3/1.6 beta glucan, or root extracts from the plant *astragalus* membranaceus or oil of oregan or carvacrol or medications, such as for example tilorone, which can improve the immunological defence systems of animals and humans against infections by organisms such as for example virus, fungus, bacteria or parasites. The doses of beta glucans needed to produce immunostimulatory effects vary among species and will also depend on the health status of the individuals and effects sought. The oral doses of beta glucans to swine and chicken are generally from 0.2 mg/kg bodyweight/day to 4 mg/kg bodyweight/day and is mixed into the feed of the animals, preferably 0.2 to 1.0 mg/kg bodyweight/day of beta glucans having a particle size of 5 micron or less. Antibacterial compounds, such as for example tylosin, bacitracin and lincomycin, can be used for the prevention of infections or for controlling or reducing infections and/or for promoting health or growth (growth promotion), and/or for decreasing mortality. As an example, tylosin may be administered for example to swine for control of proliferative enteropathies (ileitis) that is caused or associated with Lawsonia intercellularis, for improved feed efficiency and/or for improved muscle-to-fat ratio.

It has now been found that solutions containing water-soluble salt forms of formulations of RR/SS/RS/SR-ractopamine in the drinking water are suitable for administration to animals, e.g. swine, cattle, sheep, horses, chicken, and turkeys. The concentrations of a water-soluble salt form of RR/SS/RS/SR-ractopamine in the drinking water are within the limits stated above for drinking water containing RR/SR-ractopamine for swine, cattle, sheep, horses, chicken, and turkeys.

In a further embodiment, the present invention provides methods for treatment with RR/SR-ractopamine of overweight or obese companion animals. According to this embodiment, the present invention provides a method for reducing excessive fat in overweight or obese companion animals, by administering to the subject in need thereof, an effective amount of a preparation containing RR/SR-ractopamine. The terms "obese companion animal", "obese dogs", "obese cats" are herein defined as dogs or cats being 20% or more overweight as compared with the normal weight of animals of the same species, strain and age. An "overweight" dog or cat is herein refined as an animal being at least 10% heavier than the normal weight of animals of the same species, strain and age.

The invention also relates to a method of treating obesity in companion animals, said method comprises administering an adrenergic beta-receptor agonist, such as RR/SR-ractopamine together with at least one additional compound of therapeutic value, in particular an anti-obesity drug, such as for example a cannabinoid-1 receptor antagonist, such as for example rimonabant, or a microsomal triglyceride transfer protein inhibitor, such as for example mitratapide or dirlotapide. Dirlotapide is presently marketed in the US as single-drug therapy for the treatment of obesity in companion animals under the name SLENTROL®, Pfizer. As an alternative to simultaneous co-administration of ractopamine+another active anti-obesity drug, the treatment of obese animals may alternate between therapeutically effective doses of for example ractopamine or an isomeric mixture thereof and dirlotapide, which will have the added advantage of improved therapy by avoiding or decreasing receptor down-regulations or the effects thereof. The doses of the therapeutic compounds depend on the species, the subspecies, the size of the animal and the results sought and the efficacy of the compounds. Thus, oral doses of 0.1 to 100 mg of RR/SR-ractopamine, one to four times daily will be an adequate dose-range for the treatment of most companion animals and oral doses of a cannabinoid-1 receptor antagonist may range from 1 mg to 100 mg, one to four times daily. The therapeutic dose of a cannabinoid-1 receptor antagonist, such as for example rimonabant, may range from 0.05 mg to 50 mg one to four times daily and the daily dose of a microsomal triglyceride transfer protein inhibitor, such as for example mitratapide may range from 0.05 mg to 50 mg. The recommended dose of the microsomal triglyceride transfer protein dirlotapide (Slentrol®, Pfizer) is up to 1 mg/kg body weight, twice daily and has to be adjusted after about 2 months when used as single-drug therapy in obese dogs (www.pfizerah.com/slentrol, which document is hereby incorporated in its entirety by reference). Reduction of obesity is known to improve health in all obese mammals and the therapy suggested here would be useful also in humans. The invention may also provide prophylactic treatment to mammals with hereditary or environmental risks for the development of obesity. Thus the present invention provides both symptomatic and prophylactic treatment for animals and humans suffering from obesity or being at risk for developing obesity. Other adrenergic beta-receptor agonists, such as for example RR/SS/RS/SR-ractopamine, R-salbutamol and zilpaterol may also cause weight loss in overweight or obese companion animals and, when administered in the dose-range described above for RR/SR-ractopamine, will also have therapeutic value in the treatment of obesity and may successfully be combined with other anti-obesity drugs, as described above for RR/SR-ractopamine.

It has also been found that RR/SR-ractopamine and particularly water-soluble salts thereof are well suited for administration in drinking water to animals. The biologically active forms of RR/SS/RS/SR-ractopamine or RR/SR-ractopamine are also suitable for administration in implanted reservoirs, as for example reservoirs to be implanted into the rumen of cattle or sheep, as described in for example U.S. Pat. Nos. 6,855,334 and 6,974,587, which patents are hereby included in their entirety by reference.

Eutectic mixtures of the RR and SR-enantiomers may have certain physicochemical, therapeutic, financial or manufacturing advantages over RR/SR-mixtures containing approximately 50% of each isomer. Formulations containing any eutectic mixture of the RR- and SR-enantiomers of ractopamine are included in the present invention.

Compounds, such as for example ester compounds, which are metabolized to RR- and/or SR-ractopamine, may be used instead of RR/SR-ractopamine to obtain certain advantages, such as improved or extended bioavailability. All compounds, drugs or prodrugs that are metabolized or converted into RR/SR-ractopamine or pharmaceutically acceptable salts, solvates or polymorphs thereof, are part of the present invention.

In the present method, RR/SR-ractopamine can be administered by any suitable means, including parenterally, transdermally, subcutaneously, intravenously, intramuscularly, orally, topically, nasally, rectally, by inhalation or via implanted reservoirs or pellets containing the drug. A preferred route of administration is the oral route, with the drug mixed into the feed or the drinking water of animals.

When administered in the feed or in the drinking water, the active ingredient is initially prepared as a premix that is in the form of a powder or a granulate, by methods that are well known to those skilled in the art. Powders may be sifted and/or milled as is also known to those skilled in the art. The powder/granulate can be sold as is or can be mixed with diluents into premix solutions. The premix materials may contain other active ingredients, such as for example certain antibacterial agents or formulation excipients, and can be used for final mixing into the animal feed or drinking water by the end-user. Since both SR-ractopamine and RR-ractopamine have short biological half-lives, no withdrawal period is needed and RR/SR-ractopamine may be administered to livestock animals up to and including the day of slaughter.

The form in which the drug will be administered (e.g. injectables, inhalants, powders, granulates, tablets, capsules, solutions, emulsions, subcutaneous pellets, transdermal patches, suppositories, sprays, aerosols or reservoirs to be implanted into the rumen of cattle or sheep, etc.) will depend on the route by which it is administered. RR/SR-ractopamine, may be administered orally in tablets, granulae, powder, capsules, caplets, solutions, suspensions or similar forms. Formulations for oral use may contain the active ingredient(s) in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatine or acacia; and lubricating agents, for example, magnesium stearate, stearic acid or talc. Other pharmaceutically acceptable excipients can be colorants, flavouring agents, plasticizers, humectants etc. Tablets may be uncoated or they may be coated using known techniques, optionally to mask taste, delay disintegration and delay absorption in the gastrointestinal tract and thereby provide a sustained action over a longer period of time, such as for examples one or more days. For example, a time delay material such as glyceryl monostearate or glyceryl distearate may be employed.

Formulations for oral use of RR/SR-ractopamine may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provides the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydride, for example, polyoxyethylene stearate, polyoxyethylene sorbitol monooleate, polyoxyethylene sorbitan monooleate, etc. Suitable suspending agents are, for example, sodium carboxymethylcellulose, methylcellulose, sodium alginate etc.

Additionally, other preferred forms of administration are by inhalation or by transdermal delivery systems or subcutaneous delivery systems, which will reduce or avoid gastrointestinal metabolism and hepatic first-pass metabolism by metabolizing enzymes; such delivery systems may be designed to prolong the absorption or decrease the peak plasma drug concentration or to increase the exposure of the animal to the drug (increased AUC, meaning Area Under a Curve, where plasma drug concentration has been plotted over time).

Preparations of RR/SR-ractopamine may also be administered parenterally (intravenous, intramuscular, subcutaneous or the like) in dosage forms or formulations containing conventional, non-toxic pharmaceutically acceptable carriers and adjuvants. The formulation and preparation of such compositions is well known to those skilled in the art of pharmaceutical formulations. Additional information can be obtained in medical and pharmaceutical textbooks, such as for example Goodman & Gilman: The Pharmacological Basis of Therapeutics. Section 1. McGraw-Hill, Ed 9, ISBN 0-07-026266-7. For parenteral use, the pharmaceutical compositions according to the present invention may comprise the preparation in the form of a sterile injection. To prepare such a composition, the preparation is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl p-hydroxybenzoate, ethyl p-hydroxybenzoate or n-propyl p-hydroxybenzoate.

For parenteral administration RR/SR-ractopamine preparations may be prepared in the form of a paste or pellet and administered as an implant, often under the skin of non-edible parts of the livestock animals, such as the head or ear of livestock animal in which increase in lean meat deposition and improvement in muscle-to-fat ratio is sought.

As an alternative to a paste, pellet or subcutaneous implant, parenteral administration may involve injection of a solution, containing sufficient amount of RR/SR-ractopamine to provide the animal with 0.1 to 100 mg/day of the active ingredient.

For rectal administration, suitable dosage forms of a composition according to the present invention include suppositories (emulsion or suspension type), and rectal gelatin capsules (solutions or suspensions) containing RR/SR-ractopamine. In a typical suppository formulation, the RR/SR-ractopamine preparation is combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated.

For nasal administration, typical dosage forms of a composition according to the present invention include nasal sprays and aerosols. In a typical nasal formulation, the active ingredients are dissolved or dispersed in a suitable vehicle. The pharmaceutically acceptable vehicles and excipients and optionally other pharmaceutically acceptable materials present in the composition such as diluents, enhances, flavouring agents, preservatives etc. are all selected in accordance with conventional pharmaceutical practice in a manner understood by the persons skilled in the art of formulating pharmaceuticals.

RR/SR-ractopamine preparations according to the present invention may also be administered topically on the skin for percutaneous absorption in dosage forms or formulations containing conventionally non-toxic pharmaceutically acceptable carriers and excipients that may include microspheres and liposomes. The RR/SR-ractopamine compositions include creams, ointments, lotions, liniments, gels, hydrogels, solutions, suspensions, pastes, plasters, patches and other kinds of transdermal drug delivery systems. The RR/SR-ractopamine compositions may include emulsifying agents, antioxidants, buffering agents, preservatives, humectants, penetration enhancers, chelating agents, gelforming agents, ointment bases, perfumes and skin protective agents.

The quantity of the drug to be administered to an animal will have to be titrated for each species. In general, the doses of the RR/SR-ractopamine to be used in swine may—as an example—be 20 to 100 mg/animal/day in the feed. With a total treatment period of 28 days and 20 to 100 mg/animal/day, this corresponds to a total consumption of from about 0.5 grams to about 3 grams of RR/SR-ractopamine for each swine. The doses of the RR/SR-ractopamine preparation to be used in cattle may—as an example—be about 20 ppm of RR/SR-ractopamine in the feed and a treatment period of 28 days, which corresponds to a total consumption of about 6 grams of RR/SR-ractopamine for each animal. It is usually calculated that finishing cattle have a feed consumption of 10 kg/day. The total consumption of RR/SR-ractopamine will be decreased or increased with changes in the feed inclusion of RR/SR-ractopamine and with changes in the duration of the treatment period. The daily dose of RR/SR-ractopamine to cattle may be as high as 500 mg/animal/day. It is common and it may be found advantageous to change the feed inclusion of RR/SR-ractopamine during the treatment period and all changes in the doses administered to the animals will of course influence the total consumption per animal of active ingredient.

Since both RR-ractopamine and SR-ractopamine have short biological half-lives, no withdrawal period is needed and RR/SR-ractopamine can be administered to the animals until and including the day of slaughter.

It may be advantageous to administer RR/SR-ractopamine as an implantable subcutaneous controlled-release pellet, designed to deliver from 1 mg/day to 300 mg/day for the entire treatment period, which may last up to six or eight weeks, whereupon the animal may be slaughtered without any withholding period (drug-free days before slaughter) or with a short withholding period of one to three days. For all livestock species, the doses of RR/SR-ractopamine have to be carefully titrated and will depend on the pharmacological efficacy of the drug in the selected species or sub-species, the metabolic fate and rate of excretion of the drug in various species and sub-species, the route of administration, the size of the animal and the results sought. In general, quantities of RR/SR-ractopamine sufficient to decrease body fat, increase muscle mass, and improve feed efficiency will be administered to livestock animals. The actual dosage (quantity administered at a time) and the number of administrations per day will depend on the pharmacokinetic property of the drug and the metabolism of the drug in the body of the specific animal species and sub-species. About 10 to 3000 micrograms of RR/SR-ractopamine may be given by various forms of inhalation devices, such as metered dose inhalers and nebulizers, 0.01 to 500 milligrams may be given by the oral route (for example as powders, granulates, tablets or liquids) one to four times per day (or as ad lib daily doses to animals) and may be an adequate dose in most livestock animals to produce the desired effect. Suitable oral doses in humans include doses in the range of 0.05 mg to 5 mg once daily or said doses given repeatedly up to six times during a 24-hours period. The actual and finally titrated drug doses may be higher or lower and administration may take place more or less frequently than indicated above, as determined by clinical studies or by the caring individual, physician or veterinarian.

Sterile solutions for use in nebulizers—particularly in horses suffering from heaves are supplied in unite-dose, low-density polyethylene (LDPE) vials as a clear, colourless, sterile, often preservative-free, aqueous solution containing different doses of RR/SR-ractopamine (for example 0.63 mg, 1.25 mg, 5 mg, etc.). The doses and concentrations shown here and elsewhere in this document are examples only. Other concentrations may be manufactured for use by the caring veterinary staff. Metered dose dispensers may contain the API (RR/SR-ractopamine) as a solution or as a micronized suspension.

TABLE 1

Example of Formulation for Metered Dose Dispenser (canister)

| Formula | Quantity contained in each Metered Dose Dispenser 7.5 ml (approx. 10.5 g) |
|---|---|
| RR/SR-ractopamine (calc. as free amine) | 1.8 mg |
| Trichloromonofluoromethane | 5.197 g |
| Dichlorodifluoromethane | 5.197 g |
| Sorbitan trioleate | 0.105 g |

Each actuation may deliver 90 mcg of SR/RR-ractopamine. Multiple actuations will be given to the horse for acute treatment of airway obstruction. Alternatively, devices that deliver larger volumes of RR/SR-ractopamine can be used to horses. Metered dose dispensers may also dispense the API as a dry powder, as is well known to those skilled in the art. The formulation may also contain a steroid, as is well known to those skilled in the art. The formulation may also contain a preservative and other excipients, as is also known to those skilled in the art.

It is recognized that more than one pellet, tablet or dose may be administered to an animal to achieve the desired dose level which will provide the increase in lean meat production and improvement in lean meat to fat ratio desired. Moreover, it has been found that implants may also be administered temporarily during the animal treatment period in order to maintain the proper drug level in the animal's body.

The pharmacological side effects of RR/SR-ractopamine in high dose include tremor and tachycardia. These and other side effects may be of short duration and may be associated with peak plasma concentrations of the drug in connection with a drug overdose. These side effects can be reduced or completely avoided by admixture of the RR/SR-ractopamine formulation into the feed or the drinking water of livestock animals or by using drug delivery systems that slowly release the drug of the present invention into the systemic circulation. Such slow-release or controlled-release delivery systems include granulae, tablets, capsules, subcutaneous pellets or forms of reservoir depots with slow-release or controlled-release properties that are designed to release the active ingredient slowly or in a controlled manner.

In the methods of the present invention, RR/SR-ractopamine can be administered together with one or more other active compound(s). Compounds that improve or prolong the therapeutic effect of beta-agonists, e.g. compounds that delay or inhibit the absorption or the metabolic degradation of the compound, may also be co-administered with the adrenergic beta-receptor agonist to further improve the therapeutic activity. Other drugs such as for example other growth promoting agents and antibacterial compounds or immunostimulating compounds may be combined with the selected drug of the present invention to obtain improved health of the animal or improved growth-promotant activity of the formulation.

Antibacterial agents may be used together with compounds of the present invention in order to prevent or control infections by bacteria, virus, fungus and/or parasites or to improve on possible antibacterial effects of the compounds of the present invention. Antibacterial compounds also have growth promoter activity by unknown mechanisms of action. Thus antibacterial agents may increase or promote or potentiate the effects of the compounds of the present invention on fat reduction, muscle growth and/or feed efficiency.
Chemical Stability of Isolated Ractopamine Isomers.

| Methodology. | |
|---|---|
| Test Method: | HPLC |
| Instruments: | Shimadzu SCL-10 A Sysyem Controller |
| | Shimadzu SPD-10 A UV-VIS Detector |
| | Shimadzu SIL-10 AD vp Auto Injector |
| | Shimadzu LC 10 AT Pump |
| | Shimadzu Class VP 5.03 Software |
| Column: | Chiralpak AD 250/4.6/10 |
| Length × ID: | 250 × 4.6 |
| Wavelength: | 210 nm |
| Inj. Volume: | 10 µl |
| Eluent: | Hexane - isopropanol (80:20) |
| Solvent: | Hexane - isopropanol (70:30) |
| Sample Preparation: | Treat 10 mg of product with 0.01 ml of (R)-(−)-menthyl chloroformate in mixture of 0.8 ml of dichloromethane and 0.5 ml of 5% $Na_2CO_3$. Allow the reaction to proceed by stirring at rt for 10 min. Take 0.1 ml of organic base, remove the solvent in $N_2$ flow and dissolve the residue in 1 ml of solvent. |
| Integration: | 1-50 min |
| Retention Times: | RR-isomer 14 min |
| | SR-isomer 17 min |
| | SS-isomer 18 min |
| | RS-isomer 36 min |

Experimental.

Using the test method described above, the optical stability of the ractopamine isomers was studied. In tests of RR-ractopamine, where said enantiomer was dissolved in water at room temperature, it was found that within 6 hours, optically pure RR-ractopamine had transformed into a mixture containing 86.8 percent RR-ractopamine and 13.2 percent SR-ractopamine. The epimerization was temperature-dependent and was accelerated by incubation at 35 to 42 degrees centigrade. The epimerization was also dependent on acidity and at pH 1 and body temperature the epimerization was significantly enhanced. Epimerization of SR-ractopamine into a mixture consisting of SR-ractopamine and RR-ractopamine proceeded at the same rate as the epimerization of RR-ractopamine. To avoid epimerization, a single enantiomer of ractopamine as for example RR-ractopamine has to be kept under strictly dry conditions and must not be exposed to humidity, such as normal humidity indoors or outdoors. Thus, an optically pure enantiomer of ractopamine, such as for example optically pure RR-ractopamine may only exist as long as the compound is kept under dry and cool conditions. Furthermore, it was established that the epimerization takes place at the "OH-site" (FIG. 1), while the "Me-site" of the ractopamine isomers was found to be optically stable.
Biological Effects
Background.

The growth promotant activity of ractopamine has been demonstrated in various livestock species. See for example: Watkins et al., 1994; Mills et al., 2002; and Marchant-Forde et al. 2003, which publications are hereby included in their entirety by reference.

To those skilled in the art of pharmacology, it is known that synthetic adrenergic beta-receptor agonists have numerous effects that are similar to endogenous adrenergic beta-receptor agonists, of which adrenaline and noradrenaline are the most well known. Three main types of adrenergic beta-receptors have been described: Stimulation of adrenergic beta-1 receptors leads—for example—to increased heart rate, increased cardiac contractility and increased blood pressure. Stimulation of adrenergic beta-2 receptors leads—for example—to increased lipolysis in adipocytes and relaxation of various types of smooth muscles, such as bronchial smooth muscle. Adrenergic beta-3-adrenergic receptors are—for example—involved in the regulation of lipolysis and thermogenesis.

Fat cells (adipocytes) have adrenergic beta-1, beta-2 and beta-3 receptors and stimulation of these receptors usually leads to lipolysis, which means that the fat content of the cells is decreased. Pharmacologically, this is a well known and fairly simple process, starting by adrenergic beta-receptor agonists activating adrenergic beta-receptors, leading to activation of G-protein-coupled receptors and adenylcyclase activation, causing increased production of cAMP, which in turn activates protein kinase A, which is activating the enzyme lipase in the adipocytes. Lipase is causing the breakdown of the triglycerides into glycerol and free fatty acids (see textbooks in pharmacology, such as Goodman-Gilman). Adrenergic beta-receptor stimulation is also known to increase muscle mass by a mechanism that is believed to involve inhibition of protein breakdown in the continuously ongoing process of formation and degradation of muscle proteins (Bardsley et al., 1992, which publication is hereby included in its entirety by reference.) Other mechanism for the increase in muscle mass have been suggested and involve an induction of increased synthesis of proteins by adrenergic beta-receptor activation. Thus, stimulation of adrenergic beta-receptors at various locations in the body will lead to decreased fat deposits and increased muscle mass.

Ractopamine stimulates adrenergic beta-1 and beta-2 receptors, but neither RR/SS/RS/SR-ractopamine nor any of the ractopamine isomers had significant affinity for adrenergic beta-3 receptors in the present studies.

In receptor binding studies, it has now been found that RR-ractopamine, followed by RS-ractopamine have the highest affinity for adrenergic beta-receptors among the four ractopamine isomers. Also, RR/SR-ractopamine had very substantial affinity for adrenergic beta-receptors. The single isomers of ractopamine have previously been tested biologically, but the chiral configurations of the single isomers RS- and SR-ractopamine are not well defined in many publications, making it difficult or impossible to differentiate between the effects of the RS and the SR enantiomers.

Those skilled in the art of pharmacology avoid linking in vivo activity of adrenergic beta-agonist activation directly to receptor affinity of drugs, since the ultimate effects in vivo depend not only on receptor affinity, but also on the intracellular signalling, as described for lipolysis above and the availability and composition of the available receptor population in various organs. The complicated situation in various organs can be exemplified with the availability of β-1 and β-2 receptors in the human heart, where, under normal circumstances, the distribution of adrenergic beta-receptors are approximately 77% β-1 receptors+23% β-2 receptors and during heart failure the human heart has less β-1 receptors than normal, and as a result the beta-receptor population in the failing heart may consist of about 60% β-1 receptors+about 40% β-2 receptors (Bristow et al., 1986, which publication is hereby included in its entirety by reference.) Since also the target cells for RR/SR-ractopamine have both β-1 receptors and β-2 receptors, a combined beta-1/beta-2 receptor agonist, such as RR/SR-ractopamine, may have advantages over a selective beta-1 or a selective beta-2 agonist. Adrenergic beta-receptors may also be down-regulated in selected organs upon repeated stimulation with an adrenergic agonist. The terms "down-regulated" and "down-modulated" refer to the fact that individual receptors may disappear from the cell membrane, probably by internalisation into the cell. A decreased beta-receptor density by beta-adrenergic stimulation was described by Spurlock et al., 1994, who found that the concentration of adrenergic beta-receptors in adipose tissue could be reduced by 50% by exposing animals to ractopamine, (Spurlock et al., 1994, which publication is hereby included in its entirety by reference.)

The inhibition constants (herein called "affinity") were calculated using the Cheng Prusoff equation, $(K_i=IC_{50}/(1+(L/K_D))$, where L=concentration of radioligand in the assay, and $K_D$=affinity of the radioligand for the receptor.

TABLE 3

General procedures for receptor binding studies.

| Assay | Origin | Reference Compound | Bibliography |
|---|---|---|---|
| $\beta_1$ (h) | human recombinant (HEK-293 cells) | atenolol | Levin et al. (2002) |
| $\beta_2$ (h) | human recombinant (CHO cells) | ICI 118551 | Joseph et al. (2004) |
| $\beta_3$ | rat adipose tissue | cyanopindolol | Sillence et al. (1993) |

TABLE 4

Experimental conditions for receptor binding studies.

| Assay | Ligand | Conc. | Non Specific | Incubation | Method of Detection |
|---|---|---|---|---|---|
| $\beta_1$ (h) | [$^3$H](−)CGP 12177 | 0.15 nM | alprenolol (50 µM) | 60 min./22° C. | Scintillation counting |
| $\beta_2$ (h) | [$^3$H](−)CGP 12177 | 0.2 nM | alprenolol (50 µM) | 120 min./22° C. | Scintillation counting |
| $\beta_3$ | [$^{125}$I]CYP (+1 µM (−)propranolol) | 0.3 nM | (−)propranolol (1 mM) | 90 min./37° C. | Scintillation counting |

EXAMPLES

Example 1

Optical Purity of Ractopamine Enantiomers

Using the analytical methodology previously described, studies have now been performed to determine the optical purity of the single enantiomers that were made by us and used in our studies. The results are shown in Table 2.

TABLE 2

Optical purity of ractopamine enantiomers.

| Test article | RR | SS | RS | SR |
|---|---|---|---|---|
| RR-ractopamine | 97.8% | — | — | 2.2% |
| SS-ractopamine | — | 96.7% | 3.3% | — |
| RS-ractopamine | 0.3% | 0.3% | 99.2% | 0.3% |
| SR-ractopamine | 0.2% | 0.7% | 0.3% | 98.8% |

Example 2

Affinity of Ractopamine Isomers to Adrenergic Beta-Receptors

Adrenergic beta-receptor binding studies were conducted utilizing human recombinant receptors and as described in the tables X and Y below. The specific binding of the radioactive ligand to the receptor was defined as the difference between total binding and nonspecific binding, determined in the presence of excess unlabelled ligand.

TABLE 5

Test results. Affinity (Ki) for adrenergic β-receptors.

| Compound | $\beta_1$ | $\beta_2$ | $\beta_3$ |
|---|---|---|---|
| Ractopamine | 2.6E−07 | 3.0E−07 | >1E−05 |
| RR-ractopamine | 1.1E−07 | 1.3E−07 | >1E−05 |
| SS-ractopamine | >1E−04 | >1E−04 | >1E−04 |
| RS-ractopamine | 8.4E−07 | 3.1E−07 | >1E−05 |
| SR-ractopamine | 1.0E−06 | 1.0E−06 | >1E−05 |
| R-salbutamol | 3.3E−06 | 3.7E−07 | >1E−04 |

R-salbutamol was a gift from Dr. Y. Hamied, Cipla, Mumbai, India.

Conclusions from Receptor Binding Studies:

Ractopamine had similar affinity for human $\beta_1$ and $\beta_2$ receptors and had no or minimal affinity for human $\beta_3$ receptors.

RR-ractopamine was approximately twice as active as RR/SS/RS/SR on both $\beta_1$ and $\beta_2$ receptors. RR-ractopamine had no or minimal affinity for $\beta_3$ receptors.

SS-ractopamine had no affinity for any of the tested β-receptors.

RS-ractopamine had slightly higher affinity for $\beta_2$ than $\beta_1$ receptors and had no or minimal affinity for $\beta_3$ receptors.

SR-ractopamine had the same affinity for $\beta_1$ and $\beta_2$ receptors and was about 100 times less active than RS-ractopamine on both receptors. No or minimal affinity for $\beta_3$ receptors.

It should be noted that receptor binding studies do not reflect the functional activities of ractopamine isomers and as demonstrated by Mills et al., 2003a, SR-ractopamine is significantly more active than RS-ractopamine in activating adenyl cyclase and lipolysis in porcine adipocytes.

Example 3

Neuropharmacological Studies

A series of neuropharmacological profile studies (also called "Irwin tests") are being performed in mice. The test articles were prepared in 0.5% (w/v) an aqueous methylcellulose solution (viscosity of 2% aqueous solution at 20° C.: 400 centipoises). At the end of a habituation period of at least five days, the non-fasted mice were gathered in groups of 6 animals, weighed and administered by gavage with a volume of 10 ml/kg of either vehicle or the reference compound R-salbutamol (Cipla Batch #HX0247; gift from Dr. Y. Hamied).

The testing procedure involved an initial phase of undisturbed observation and a later manipulative phase. All observations were made by a trained and experienced technician. The tests were performed in a blinded manner as the observing technician was unaware of the dosing (vehicle, reference compound, or test article). The animal's assessment started by observing its undisturbed behaviour in housing and included body position, locomotor activity, bizarre behaviour, respiration, tremors, twitches, convulsion, etc. Thereafter the animal was transferred by tail to the working table for the manipulative phase, where observations were made regarding spatial locomotion, gait, aggressiveness, touch-escape, escape response, body tone, grip strength, tail-pinch testing, urination-defecatio, pupil size, catalepsy, etc. The occurrence of any unexpected state was noted. The animals were tested at 60 min, 120 min and 24 hrs after dosing and criteria included behavioral, neurological, autonomic and toxicity changes in comparison with groups of mice treated with vehicle or with R-salbutamol that does not cause stress in livestock animals (Marchant-Forde et. al. 2003).

The results are expressed for each group as the number of animals displaying behavioural changes versus control group at each observation time and differences between groups are considered significant at $P<0.05$.

Results to date demonstrate that R-salbutamol does not induce stress in mice, thereby supporting the findings in pigs by London et al (London et al., 2005), while RR/SS/RS/SR-ractopamine is causing altered behaviour indicating induction of stress, thereby supporting the findings in pigs by Marchant-Forde et al. (2003). The results with the reference compounds are therefore validating the test methodology. Results to date also demonstrate that neither the RR-isomer nor the SR-isomer of ractopamine caused behavioural changes in the laboratory animals, which is considered as an indication that no drug-induced stress is expected by these enantiomers in livestock animals.

Example 4

Spontaneous Motor Activity

Spontaneous motor activity studies were performed in mice being administered test articles orally. Groups of six animals were placed in a new environment (cage) under strictly controlled conditions. Motor activity was measured electronically. Test articles: RR/SS/RS/SR-ractopamine, RR/SR-ractopamine, R-salbutamol, vehicle. As known by those skilled in the art, increased stress will produce increased motor activity in mice. When compared with control groups that were dosed orally with the vehicle only, there were no statistically significant effects of RR/SR-ractopamine on spontaneous motor, while spontaneous motor activity was significantly increased by pre-treatment with RR/SS/RS/SR-ractopamine. R-salbutamol did not cause increased activity. It has previously been shown in livestock animals that ractopamine, but not R-salbutamol is causing stress in pigs (Marchant-Forde et al., 2003 and London et al, 2005.) Thus the results from test of the reference compounds ractopamine and R-salbutamol verify the validity of the present test methodology.

Conclusions from biological tests: RR/SR-ractopamine has potent adrenergic activity. Optically pure SS-ractopamine has no affinity for adrenergic beta-receptors. RR/SS/RS/SR-ractopamine is causing increased motor activity, indicative of CNS-mediated stress, while RR/SR-ractopamine does not demonstrate increased motor activity, which is indicative of this compound not causing CNS-mediated stress.

EQUIVALENTS

Although the present invention has been described with reference to certain preferred embodiments, many variations and modifications may be made within the scope of the broad principles of the invention. Hence, it is intended that the preferred embodiments and all of such variations and modifications be included within the scope and spirit of the invention, as defined by the claims.

The invention claimed is:

1. A method of promoting weight loss in an animal or human, which comprises administering thereto an effective amount of RR/SR-ractopamine or pharmaceutically acceptable salts or solvates thereof.

2. The method of claim 1, wherein said administration minimizes or eliminates side effects caused by RR/SS/RS/SR-ractopamine.

3. The method of claim 2, wherein said side effect is stress.

4. The method of claim 2, wherein said side effect is tachycardia.

5. The method of claim 2 wherein said side effect is increased morbidity.

6. The method of claim 2, wherein said side effect is a decrease in meat quality.

7. The method of claim 1, wherein RR/SR-ractopamine contains from 46 percent to 54 percent of one of either the RR or the SR isomer and from 54 percent to 46 percent of the other of the RR or the SR isomer.

8. The method of claim 1, wherein RR/SR-ractopamine contains from 55 percent to 79 percent of one of either the RR or the SR isomer and from 45 percent to 21 percent of the other of the RR or the SR isomer.

9. The method of claim 1, wherein the effective amount of RR/SR-ractopamine or a pharmaceutically acceptable salt or solvate thereof is administered to said animal as a feed additive, the concentrations of RR/SR-ractopamine being from 1 ppm to 500 ppm.

10. The method of claim 1, wherein an effective amount of RR/SR-ractopamine or a pharmaceutically acceptable salt or solvate thereof is administered in drinking water, the concentrations of RR/SR-ractopamine being from 1 ppm to 500 ppm in said drinking water.

11. The method of claim 1, wherein RR/SR-ractopamine or a pharmaceutically acceptable salt thereof is administered in combination with an effective amount of at least one antibacterial compound.

12. The method of claim 1, wherein RR/SR-ractopamine or a pharmaceutically acceptable salt thereof is administered in combination with an effective amount of at least one immune-stimulating compound.

* * * * *